US007575929B2

(12) United States Patent
Bar-Or et al.

(10) Patent No.: US 7,575,929 B2
(45) Date of Patent: Aug. 18, 2009

(54) DIAGNOSIS OF MULTIPLE SCLEROSIS WITH DIKETOPIPERAZINES

(75) Inventors: David Bar-Or, Englewood, CO (US); Raphael Bar-Or, Denver, CO (US)

(73) Assignee: DMI Life Sciences, Inc., Greenwood Village, CO (US)

( * ) Notice: Subject to any disclaimer, the term of this patent is extended or adjusted under 35 U.S.C. 154(b) by 216 days.

(21) Appl. No.: 10/679,699

(22) Filed: Oct. 2, 2003

(65) Prior Publication Data

US 2004/0209379 A1   Oct. 21, 2004

Related U.S. Application Data

(60) Provisional application No. 60/415,908, filed on Oct. 2, 2002, provisional application No. 60/489,039, filed on Jul. 21, 2003, provisional application No. 60/503,185, filed on Sep. 15, 2003.

(51) Int. Cl.
  *G01N 33/00* (2006.01)
  *G01N 33/53* (2006.01)
(52) U.S. Cl. .......................................... 436/86; 435/7.1
(58) Field of Classification Search .................. None
  See application file for complete search history.

(56) References Cited

U.S. PATENT DOCUMENTS

| | | |
|---|---|---|
| 3,928,330 A | 12/1975 | Ramey et al. |
| 3,976,773 A | 8/1976 | Curran |
| 4,205,057 A | 5/1980 | Whitaker |
| 4,289,759 A | 9/1981 | Heavner et al. |
| 4,312,987 A | 1/1982 | Beck |
| 4,331,595 A | 5/1982 | Heavner et al. |
| 4,661,500 A | 4/1987 | Rozencwaig ................ 514/325 |
| 4,694,061 A | 9/1987 | Pfeifer |
| 4,694,081 A | 9/1987 | Miller et al. |
| 4,771,056 A | 9/1988 | Rozencwaig ................ 514/325 |
| 4,806,538 A | 2/1989 | Shimazaki et al. |
| 4,940,709 A | 7/1990 | Shimazaki et al. |
| 4,992,552 A | 2/1991 | Hubbs et al. |
| 5,047,401 A | 9/1991 | Lipsky et al. |
| 5,358,938 A | 10/1994 | Cai et al. |
| 5,418,218 A | 5/1995 | Wilber |
| 5,434,151 A | 7/1995 | Cai et al. |
| 5,463,083 A | 10/1995 | Biftu et al. |
| 5,512,544 A | 4/1996 | Wallach et al. |
| 5,538,993 A | 7/1996 | Mechoulam et al. |
| 5,543,402 A | 8/1996 | Bosies et al. |
| 5,543,503 A | 8/1996 | Chuntharapai et al. |
| 5,545,404 A | 8/1996 | Page |
| 5,550,132 A | 8/1996 | Benson et al. |
| 5,578,323 A | 11/1996 | Milstein et al. |
| 5,648,486 A | 7/1997 | Cai et al. |
| 5,693,338 A | 12/1997 | Milstein |
| 5,700,804 A | 12/1997 | Collins et al. |
| 5,703,093 A | 12/1997 | Cai et al. |
| 5,741,809 A | 4/1998 | Biftu et al. |
| 5,750,530 A | 5/1998 | Bryans et al. |
| 5,750,565 A | 5/1998 | Cai et al. |
| 5,776,892 A | 7/1998 | Counts et al. |
| 5,780,503 A | 7/1998 | Biftu et al. |
| 5,792,776 A | 8/1998 | Biftu et al. |
| 5,817,751 A | 10/1998 | Szardenings et al. |
| 5,834,032 A | 11/1998 | Song |
| 5,843,950 A | 12/1998 | Tasaka et al. |
| 5,856,323 A | 1/1999 | Cai et al. |
| 5,877,174 A | 3/1999 | Ono et al. |
| 5,883,227 A | 3/1999 | Kline et al. |
| 5,886,152 A | 3/1999 | Nakatani et al. |
| 5,919,785 A | 7/1999 | Dinsmore et al. |
| 5,932,579 A | 8/1999 | Campbell et al. |
| 5,976,569 A | 11/1999 | Milstein |
| 5,985,581 A | 11/1999 | Nixon et al. |
| 5,990,112 A | 11/1999 | Campbell et al. |

(Continued)

FOREIGN PATENT DOCUMENTS

| | | |
|---|---|---|
| CS | 254868 | 6/1987 |
| CZ | 2827.94 | 4/1996 |
| CZ | 2000-2680 | 7/2000 |
| CZ | 2000-2681 | 7/2000 |
| DE | 19937721 | 2/2001 |
| EP | 0043219 | 1/1982 |
| EP | 0 214 557 A2 | 3/1987 |
| EP | 0 214 557 A3 | 3/1987 |
| EP | 0216746 | 4/1987 |
| EP | 0493812 | 7/1992 |

(Continued)

OTHER PUBLICATIONS

Purves, Dale, et al (Eds.), Neuroscience, 2001, Sinauer Associates, Inc., 2nd Edition, pp. 75, 367, 400, and 403.*
Andreasen et al. Cerebrospinal fluid beta-amyloid(1-42) in Alzheimer disease: differences between early- and late-onset Alzheimer disease and stability during the course of disease. Arch. Neurol. Jun;56(6):673-80, 1999.*
Michell et al. Biomarkers and Parkinson's Disease. Brain. Aug; 127: 1693-1705, 2004.*
Vogel et al. Dissminated tumor cells—Their detection and significance for prognosis of gastrointestianl and pancreatic carcinomas. Virchows Arch 439:109-117, 2001.*

(Continued)

*Primary Examiner*—Daniel E. Kolker
*Assistant Examiner*—Gregory S Emch
(74) *Attorney, Agent, or Firm*—Sheridan Ross P.C.

(57) ABSTRACT

The present invention relates to the diagnosis and monitoring of diseases and conditions by quantifying markers, including degradation products of disease-associated proteins, such as diketopiperazines composed of the two N-terminal amino acids or the two C-terminal amino acids of such proteins. The methods are useful for diagnosing or monitoring various diseases, including multiple sclerosis, Alzheimer's disease and ischemia. The invention further provides binding partners specific for the markers and compositions and kits for conducting the methods of the invention.

5 Claims, 2 Drawing Sheets

U.S. PATENT DOCUMENTS

| | | |
|---|---|---|
| 6,034,057 A | 3/2000 | Dutta |
| 6,034,221 A | 3/2000 | Berezenko et al. |
| 6,060,452 A | 5/2000 | Green et al. |
| 6,090,780 A | 7/2000 | Prasad .................... 514/11 |
| 6,096,737 A | 8/2000 | Loder ..................... 514/217 |
| 6,099,856 A | 8/2000 | Milstein et al. |
| 6,107,050 A | 8/2000 | Alkon et al. |
| 6,180,616 B1 | 1/2001 | Fukunaga |
| 6,222,029 B1 | 4/2001 | Edwards et al. |
| 6,248,363 B1 | 6/2001 | Patel et al. |
| 6,262,119 B1 | 7/2001 | Ferrante et al. |
| 6,265,535 B1 | 7/2001 | Greene et al. |
| 6,358,957 B1 | 3/2002 | Fukumoto et al. |
| 6,395,774 B1 | 5/2002 | Milstein |
| 6,441,172 B1 | 8/2002 | Nefzi et al. |
| 6,461,875 B1 | 10/2002 | Bar-Or et al. .............. 436/536 |
| 6,475,743 B1 | 11/2002 | Bar-Or et al. .............. 435/7.1 |
| 6,492,179 B1 | 12/2002 | Bar-Or et al. .............. 436/74 |
| 6,541,224 B2 | 4/2003 | Yu et al. |
| 6,555,543 B2 | 4/2003 | Bar-Or et al. ......... 514/255.02 |
| 6,635,649 B2 | 10/2003 | Teng et al. |
| 6,677,473 B1 | 1/2004 | Madison et al. |
| 6,689,765 B2 | 2/2004 | Baroudy et al. |
| 6,815,214 B2 | 11/2004 | Boyce et al. |
| 6,967,202 B2 | 11/2005 | Rao et al. |
| 7,026,322 B2 | 4/2006 | Hayashi et al. |
| 2003/0153575 A1 | 8/2003 | Orme et al. |
| 2003/0187226 A1 | 10/2003 | Goodey et al. |
| 2003/0225103 A1 | 12/2003 | Bar-Or et al. |
| 2004/0038865 A1 | 2/2004 | Gelber et al. |
| 2004/0132738 A1 | 7/2004 | Teng et al. |
| 2005/0096323 A1 | 5/2005 | Cheng et al. |
| 2005/0119177 A1 | 6/2005 | Bar-Or et al. |
| 2005/0249681 A1 | 11/2005 | Heidenfelder et al. |

FOREIGN PATENT DOCUMENTS

| | | |
|---|---|---|
| EP | 0557388 | 9/1993 |
| EP | 610943 | 8/1994 |
| EP | 0655060 | 5/1995 |
| EP | 0 835 660 A1 | 4/1998 |
| EP | 939124 | 9/1999 |
| FR | 2717484 | 9/1995 |
| GB | 2263109 | 7/1993 |
| JP | 59-73574 | 4/1984 |
| JP | 63290868 | 11/1988 |
| JP | 01013075 | 1/1989 |
| JP | 3176478 | 7/1991 |
| JP | 08277203 | 10/1996 |
| JP | 10-226615 | 8/1998 |
| JP | 10245315 | 9/1998 |
| JP | 2000327575 | 11/2000 |
| NZ | 033544 | 8/2001 |
| NZ | 335544 | 8/2001 |
| RU | 2112242 C1 | 5/1998 |
| RU | 2125728 C1 | 1/1999 |
| RU | 2128840 C1 | 4/1999 |
| WO | WO 91/14378 | 10/1991 |
| WO | WO 93/08815 | 5/1993 |
| WO | WO 94/04512 | 3/1994 |
| WO | WO 94/04513 | 3/1994 |
| WO | WO 94/04537 | 3/1994 |
| WO | WO 94/20063 | 9/1994 |
| WO | WO 95/18610 | 7/1995 |
| WO | WO 96/00212 | 1/1996 |
| WO | WO 96/00391 | 1/1996 |
| WO | WO 96/10396 | 4/1996 |
| WO | WO 97/12625 | 4/1997 |
| WO | WO 97/36888 | 10/1997 |
| WO | WO 97/48685 | 12/1997 |
| WO | WO 98/40748 A1 | 9/1998 |
| WO | WO 99/40931 | 8/1999 |
| WO | WO 99/49865 | 10/1999 |
| WO | WO 99/51720 | 10/1999 |
| WO | WO 00/20454 | 4/2000 |
| WO | WO 00/20840 A1 | 4/2000 |
| WO | WO 00/57187 | 9/2000 |
| WO | WO 01/34586 | 5/2001 |
| WO | WO 02/11676 | 2/2002 |
| WO | WO 02/12201 | 2/2002 |
| WO | WO 02/059604 | 8/2002 |
| WO | WO 02/062797 | 8/2002 |
| WO | 2004034060 A2 | 4/2004 |
| WO | 2004/054498 | 7/2004 |
| WO | 2005/011699 | 2/2005 |

OTHER PUBLICATIONS

Skates et al. Molecular markers for early detection of renal carcinoma: investigative approach. Clin Cancer Res. Sep. 15;10(18 Pt 2):6296S-301S, 2004.*

Bunn. Early detection of lung cancer using serum RNA or DNA markers: ready for "prime time" or for validation?J Clin Oncol. Nov. 1;21(21):3891-3, 2003.*

Shaw et al. Future of early detection of lung cancer: the role of mouse models.Clin Cancer Res. Jul. 1;11(13 Pt 2):4999s-5003s, 2005.*

Bielekova et al. Development of biomarkers in multiple sclerosis. Brain. Jul. 2004;127(Pt 7):1463-78. Epub Jun. 4, 2004.*

Rinaldi et al. Immunological markers in multiple sclerosis: tackling the missing elements. Neurol Sci. Dec. 2005;26 Suppl 4:S215-7.*

Kuenz et al. Plasma levels of soluble adhesion molecules sPECAM-1, sP-selectin and sE-selectin are associated with relapsing-remitting disease course of multiple sclerosis. J Neuroimmunol. Oct. 2005;167(1-2):143-9.*

Esposito et al., "The Solution Structure of the C-Terminal Segment of Tau Protein," *Journal of Peptide Science* 2000, 6:550-559.

Gamblin et al., "Tau Polymerization: Role of the Amino Terminus," *Biochemistry* 2003, 42(7):2252-2257.

Crowe et al., "The N Terminal Region of Human Tau is Present in Alzheimer's Disease Protein A68 and is Incorporated into Paired Helical Filaments," *American Journal of Pathology* 1991, 139(6):1463-1470.

Berry et al., "Inhibition of Tau Polymerization by its Carboxy-Terminal Caspase Cleavage Fragment," *Biochemistry* 2003, 42:8325-8331.

Abraha et al., C-terminal inhibition of tau-assembly in vitro and in Alzheimer's disease, *Journal of Cell Science* 2000, 113:3737-3745.

Bar-Or et al., "An Analog of the Human Albumin N-Terminus (Asp-Ala-His-Lys) Prevents Formation of Copper-Induced Reactive Oxygen Species," *Biochemical and Biophysical Research Communications* 2001, 284(3):856-862.

Bar-Or et al., "Potential Plasma Surrogate Biomarkers for CNS Demyelinating Processes," Meeting of the 19th Congress of the European Committee for Treatment and Research in Multiple Sclerosis, Sep. 17-20, 2003 (abstract first distributed at the meeting).

Garcia-Sierra et al., "Conformational Changes and Truncation of Tau Protein During Tangle Evolution in Alzheimer's Disease," *Journal of Alzheimer's Disease* 2003, 5:65-77.

Hasegawa et al., "Protein Sequence and Mass Spectrometric Analysis of Tau in the Alzheimer's Disease Brain," *Journal of Biological Chemistry* 1992, 267(24):17047-17054.

Shutov et al., "[Diagnostic Significance of the type of In Vitro Interaction between Blood Lymphocytes and Serotonin in Multiple Sclerosis]" [Article in Russian], *Zh Nevrol Psikhiatr Im S S Korsakova* 2002, 102(4):35-38, Abstract only, from PubMed—PMID:12001663.

Lechin et al., "Plasma Neurotransmitters and Cortisol in Chronic Illness: Role of Stress," *J Medicine* 1994, 25(3-4):181-192, Abstract only, from PubMed -PMID:7996062.

Takahara et al., "Detection in Human Serum by Radioimmunoassay of Histidyl-Proline Diketopiperazine, a Metabolite of Thyrotropin-Releasing Hormone," *J Clinical Endocrinology* 1983, 56(2):312-319, Abstract only, from PubMed -PMID:6401750.

Prasad, "Bioactive Cyclic Dipeptides," *Peptides* 1995, 16:151-164.

Jicha et al., "Sequence Requirements for Formation of Conformational Variants of Tau Similar to Those Found in Alzheimer's Disease," *Journal of Neuroscience Research* 1999, 55:713-723.

Murray et al., "Role of α-Synuclein Carboxy-Terminus on Fibril Formation in Vitro," *Biochemistry* 2003, 42:8530-8540.

Steiner et al., "Histidyl Proline Diketopiperazine (Cyclo [His-Pro]) in Eating Disorders," *Neuropeptides* 1989, 14(3):185-189, Abstract only, from PubMed -PMID:2615922.

Prasad et al., "Isolation of cyclo(His-Pro)-like immunoreactivity from Human Urine and Demonstration of its Immunologic, Pharmacologic, and Physico-chemical Identity with the Synthetic Peptide," *Biochemistry Int* 1990, 21(3):425-434, Abstract only, from PubMed -PMID:2222490.

Hilton et al., Food Contains the Bioactive Peptide, Cyclo(His-Pro), *J Clinical Endocrinol Metab* 1992, 75(2):375-378, Abstract only, from PubMed -PMID:1639938.

Banks et al., "Radioactively Iodinated Cyclo(His-Pro) Crosses the Blood-Brain Barrier and Reverses Ethanol-Induced Narcosis," *American J Physiol* 1993, 264(5 Pt 1):E723-729, Abstract only, from PubMed -PMID:8498494.

Duntas et al., "A Fast Protein Liquid Chromatography (FPLC) Method for Study of Thyrotropin-releasing Hormone (TRH) and its metabolite Histidyl-Proline Diketopiperazine (CHP) in Human Blood: Degradation in Liver and Pancreatic Diseases," *Neuropeptides* 1993 25(6):357-361, Abstract only, from PubMed -PMID:8127415.

Shukla et al., "Role of Endogenous Cyclo(His-Pro) in Cold-Induced Hypothermia in the Desert Rat (Mastomys natalensis)," *Peptides* 1994, 15(8):1471-1474, Abstract only, from PubMed -PMID:7700849.

Jaspan et al., Study of Passage of Peptides Across the Blood-Brain Barrier: Biological Effects of Cyclo(His-Pro) After Intravenous and Oral Administration, *Annals of the New York Academy of Science* 1994, 739:101-107, Abstract only, from PubMed -PMID:7832464.

Wolf et al., "Identification of Cyclo(His-Pro)-Like Immunoreactivity in Human Follicular Fluid: Correlation with Steroid and Peptide Hormones," *J Soc Gynecol Investigation* 1994, 1(3):220-224, Abstract only, from PubMed -PMID:9419775.

Fragner et al., "A New Biological Contribution of Cyclo(His-Pro) to the Peripheral Inhibition of Pancreatic Secretion," *American Journal of Physiology* 1997, 273(6 Pt 1):E1127-32, Abstract only, from PubMed -PMID:9435528.

Yamada et al., "Abundance of Cyclo (His-Pro)-Like Immunoreactivity in the Brain of TRH-deficient Mice," *Endocrinology* 1999, 140(1):538-541, Abstract only, from PubMed -PMID:9886867.

Parker et al., "Evidence for the Presence of Immunoreactive Histidyl-Proline Diketopiperazine [Cyclo (His-Pro)] in the Adult Human Brain," *Peptides* 1983, 4(6):879-881, Abstract only, from PubMed -PMID:6672793.

Youngblood et al., "Bovine Serum Albumin-GABA-His-Pro-NH2: an Immunogen for Production of Higher Affinity Antisera for TRH," *J Neursci Methods* 1983, 9(4):367-373, Abstract only, from PubMed -PMID:6422166.

Lechan et al., "Thyrotropin Releasing Hormone but not Histidyl-Proline Diketopiperazine is Depleted from Rat Spinal Cord Following 5,7-Dihydroxytryptamine Treatment," *Brain Research* 1985, 326(1):152-155, Abstract only, from PubMed -PMID:3918765.

Diamanti Kandarakis et al., "Distribution and Characterization of Cyclo (His-Pro)-Like Immunoreactivity in the Human Gastrointestinal Tract," *Neuropeptides* 1985, 6(1):21-5, Abstract only, from PubMed -PMID:3990923.

Pekary et al., "In vitro Production of a TRH-Homologous Peptide and His-Pro Diketopiperazine by Human Semen," *J Androl* 1985, 6(6):379-385, Abstract only, from PubMed -PMID:3935636.

Koskinen, "Effect of Low Intravenous Doses of TRH, Acid-TRH and Cyclo (His-Pro) on Cerebral and Peripheral Blood Flows," *British Journal of Pharmacology* 1986, 67(3):509-519, Abstract only, from PubMed -PMID:3099875.

Prasad et al., "Distribution and Characterization of Cyclo (His-Pro)-Like Immunoreactivity in Human Cerebrospinal Fluid," *Biochem Biophys Res Commun* 1986, 136(2):835-842, Abstract only, from PubMed -PMID:2871837.

Kurahashi et al., ["Histidyl-Proline Diketopiperazine (HPD) a Metabolite of Thyrotripin-Releasing Hormone (TRH), Improves the Ataxic Gait in 3-Acetylpyridine (3-AP) Treated Rats"] [Article in Japanese] *No To Shineki* 1986, 38(9):893-898, Abstract only, from PubMed -PMID:3790371.

Coggins et al., "High Affinity Specific Binding of the Thyrotrophin Releasing Hormone Metabolite Histidylproline to Rat Brain Membranes," *Neuropeptides* 1987, 9(1):83-91, Abstract only, from PubMed -PMID:3104816.

Mori et al., "Specific Radioimmunoassay of Cyclo (His-Pro), a Biologically Active Metabolite of Thyrotropin-Releasing Hormone," *Endocrinology* 1981, 108(5):1995-1997, Abstract only, from PubMed -PMID:6783397.

Mori et al., "Regional Dissociation of Histidyl-Proline Diketopiperazine (Cyclo-(His-Pro)) and Thyrotropin-Releasing Hormone (TRH) in the Rat Brain," *Brain Research* 1982, 231(2):451-453, Abstract only, from PubMed -PMID:6799149.

Prasad et al., "Distribution and Metabolism of Cyclo (His-Pro): a New Member of the Neuropeptide Family," *Peptides* 1982, 3(3):591-598, Abstract only, from PubMed -PMID:6812031.

Mori et al., "Histidyl-Proline Diketopiperazine Cyclo (His-Pro): Identification and Characterization in Rat Pancreatic Islets," *Biochem Biophys Res Commun* 1983, 115(1):281-286, Abstract only, from PubMed -PMID:6351862.

Mitsuma et al., "Radioimmunoassay for Thyrotropin-Releasing Hormone Precursor Peptide, Lys-Arg-Gin-His-Pro-Gly-Arg-Arg," *Exp Clin Endocrinology* 1989, 93(1):53-60, Abstract only, from PubMed -PMID:2500352.

Gu et al., "Diketopeperazine Formation, Hydrolysis, and Epimerization of the New Dipeptide Angiotensin-Converting Enzyme Inhibitor RS-10085," *Pharm Res* 1987, 4(5):392-397, Abstract only, from PubMed -PMID:3508548.

Guerra et al., "PEGylation Prevents the N-Terminal Degradation of Megakaryocyte Growth and Development Factor," *Pharm Res* 1998, 15(12):1822-1827, Abstract only, from PubMed -PMID:9892464.

Sepetov et al., "Rearrangement, Racemization and Decomposition of Peptides in Aqueous Solution," *Peptide Research* 1991, 4(5):308-313, Abstract only, from PubMed -PMID:1802242.

Reubsaet et al., "Qualitative and Quantitative Aspects of the Degradation of Several Tripeptides Derived from the Antitumor Peptide Antagonist [Arg(6), D-Trp(7,9), MePhe(8)] Substance P[6-11]," *J Pharm Biomed Anal* 1999, 19(3-4):277-284, Abstract only, from PubMed -PMID:10704092.

Song et al., "Synergistic Antidiabetic Activities of Zinc, Cyclo (His-Pro), and Arachidonic Acid," *Metabolism* 2001 50(1):53-59, Abstract only, from PubMed -PMID:11172475.

Rosenthal et al., "Effects of Arachidonic Acid and Cyclo (His-Pro) on Zinc Transport Across Small Intestine and Muscle Tissues," *Life Sci* 2001, 70(3):337-348, Abstract only, from PubMed -PMID: 12005266.

Pandey et al., "Synthetic Peptides Corresponding to a Repetitive Sequence of Malarial Histidine Rich Protein Bind Haem and Inhibit Haemozoin Formation in vitro," *Mol Biochem Parasitol* 1997, 90(1):281-287, Abstract only, from PubMed -PMID:9497049.

Baig et al., "High Performance Liquid Chromatography as a Tool in the Definition of Abnormalities in Monamine and Tryptophan Metabolites in Cerebrospinal Fluid from Patients with Neurological Disorders," *Biomed Chromatogr* 1991, 5(3):108-112, Abstract only, from PubMed -PMID:1863084.

Monaco et al., "Plasma and cerebrospinal fluid tryptophan in Multiple Sclerosis and Degenerative Diseases," *J Neurol Neurosurg Psychiatry* 1979 42(7):640-1, Abstract only, from PubMed -PMID: 479903.

Scharpe et al., "Peptide Truncation by Dipeptidyl Peptidase IV: A New Pathway for Drug Discovery," *Verh K. Acad Geneeskd Belg.* 2001, 63(1):5-32, Abstract only, from PubMed -PMID:11284388.

Mentlein et al., "Dipeptidyl-Peptidase IV Hydrolyses Gastric Inhibitory Polypeptide, Glucagon-Like Peptide-1(7-36)amide, Peptide Histidine Methionine and is Responsible for their Degradation in Human Serum," *European Journal of Biochemistry* 1993, 214(3):829-835, Abstract only, from PubMed -PMID:8100523.

Hilton et al., "Radioimmunoassay of Cyclo(His-Pro) in Unextracted Human Plasma: Report of a Normal Range and Definition of Factors Critical for Successful Assay," *Neuropeptides* 1989, 13(1):65-70, Abstract only, from PubMed -PMID:2922107.

Iriuchijima et al., "Thyrotripin-Releasing Hormone and Cyclo (His-Pro)-Like Immunoreactivities in the Cerebrospinal Fluids of 'Normal' Infants and Adults, and Patients with Various Neuropsychiatric and Neurologic Disorders," *Life Sci.* 1987, 41(22):2419-2428, Abstract only, from PubMed -PMID:2891013.

Hilton et al., "Relationship between Plasma Cyclo (His-Pro), a Neuropeptide Common to Processed Protein-Rich Food, C-Peptide/Insulin Molar Ratio in Obese Women," *Nutr Neurosci* 2001, 4(6):469-474, Abstract only, from PubMed -PMID:11843266.

Mori et al., "Brain TRH and Cyclo (His-Pro) and Brain Protein in the Newborn Rat are Altered by Maternal Liquid Protein Feeding," *Life Sci* 1983, 32(14):1607-1612, Abstract only, from PubMed -PMID: 6403790.

Mori et al., ["TRH and Cyclo (His-Pro) Concentrations in the Young Rat Brain are Altered by a Liquid Protein Diet]" [Article in Japanese], *Nippon Naibunpi Gakkai Zasshi* 1987, 63(7):846-852.

Mori et al., "Alteration by Liquid Protein Diet of TRH and Cyclo(His-Pro) in the Young Rat Brain," *Res. Commun Chem Pathol Pharmacol* 1985, 47(1):157-160, Abstract only, from PubMed -PMID:392073.

Goolcharran et al., "Comparison of the Rates of Deamidation, Diketopiperazine Formation and Oxidation in Recombinant Human Vascular Endothelial Growth Factor and Model Peptides," *AAPS PharmSci* 2000, 2(1)E5, Abstract only, from PubMed -PMID: 11741221.

Moss et al., "Kinetics and Mechanism of the Facile Cyclization of Histidyl-Prolineamide to Cyclo (His-Pro) in Aqueous Solution and the Competitive Influence of Human Plasma," *J Pharm Pharmacol* 1990, 42(1):7-12, Abstract only, from PubMed -PMID:1969958.

Hilton et al., "Identification and Characterization of Cyclo (His-Pro)-Like Immunoreactivity in Amniotic Fluid," *Peptides* 10(2):299-301, Abstract only, from PubMed -PMID:2755872.

Bhargava et al., "Inhibition of Neuroleptic-Induced Dopamine Receptor Supersensitivity by Cyclo (Leu-Gly)," *Pharmacol Biochem Behav* 1980, 13(5):633-636, Abstract only, from PubMed -PMID: 7443732.

Leduque et al., "Histidyl-Proline Diketopiperazine (His-Pro DKP) Immunoreactivity is Present in the Glucagon-Containing Cells of the Human Fetal Pancreas," *J Clin Invest* 1987, 79(3):875-880, Abstract only, from PubMed -PMID:3102558.

Battersby et al., "Diketopiperazine Formation and N-Terminal Degradation in Recombinant Human Growth Hormone," *Int J Peptide Protein Res* 1994, 44(3):215-222, Abstract only, from PubMed -PMID: 7822097.

Bhargava et al., "Inhibition of Neuroleptic-Induced Dopamine Receptor Supersensitivity by Cyclo (Leu-Gly)," *Pharmacol. Biochem Behav* 1980, 13(5):633-636, Abstract only, from PubMed -PMID: 7443732.

Yanagisawa et al., "The Subcellular and Organ Distribution and Natural Form of Histidyl-Proline Diketopiperazine in Rat brain Determined by a Specific Radioimmunoassay," *J Biol Chem* 1980, 255(21):10290-10294, Abstract only, from PubMed -PMID: 7430126.

Hoffman et al., "An Enzymatically Stable Peptide with Activity in the Central Nervous System: Its Penetration Through to Blood-CSF Barrier," *Brain Res.* 1977, 122(1):87-94, Abstract only, from PubMed -PMID: 837226.

Meester et al., "In Vivo Inhibition of Dipeptidyl Peptidase IV Activity by Pro-Pro-diphenyl-phosphonate (Prodipine)", *Biochemical Pharmacology* 1997, 54:173-179.

Prasad et al., "Thermoregulation in rats: opposing effects of thyrotropin releasing hormone and its metabolite histidyl-proline diketopiperazine," *Biochem Biophys Res. Commun.* 1978, 85(4):1582-187.

Wilber et al., "Histidyl-proline diketopiperazine: a potent and chronic appetite-inhibiting neuropeptide," *Trans Assoc. Am Physicians* 1986, 99:245-249.

Wilber et al., "Endogenous histidyl-proline diketopiperazine [cyclo (His-Pro)]: a potential satiety neuropeptide in normal and genetically obese rodents," *Trans Assoc Am Physicians* 1983, 96:131-136.

Bhargava, Inhibition of abstinence syndrome in opiate dependent mice by cyclo (His-Pro), *Life Sci* 1981, 28(11):1261-1267.

Bhargava, "The effects of thyrotropin releasing hormone and histidyl-proline diketopiperazine on delta-9-tetrahydrocannabinol-induced hypothermia," *Life Sci* 1980, 26(11):845-850.

Bhargava, "Antagonism of ketamine-induced anesthesia and hypothermia by thyrotropin releasing hormone and cyclo (His-Pro)," *Neuropharmacology* 1981, 20(7):699-702.

Mori et al., "Histidyl-Proline Diketopiperazine cyclo (His-Pro): measurement by radioimmunoassay in human blood in normal subject and in patients with hyper- and hypothyroidism," *Biochem Biophys Res Commun* 1982, 109(2):541-547.

Luca et al., "Determination of serotonin content and ceruloplasmin activity, of blood and CSF amino acid level in multiple sclerosis," *Neurol Psychiatr (Bucur)* 1986, 24(3):153-159.

Mori et al., "Distribution of histidyl-proline diketopiperazine [cyclo (His-Pro)] and thyrotropin-releasing hormone (TRH) in the primate central nervous system," *Brain Res* 1982, 245(1):183-186.

Montine et al., Cerebrospinal Fluid Ab42, Tau, and F2-Isoprostane Concentrations in Patients with Alzheimer Disease, Other Dementias, and in Age-Matched Controls, Acrch Pathol Lab. Med, Apr. 2001, vol. 125, pp. 510-512.

Wennemers et al., Diketopiperazine Receptors: A Novel Class of Highly Selective Receptors for Binding Small Peptides, Chem. Eur. J. 2001, vol. 7, No. 15, pp. 3342-3347.

Prakash et al., Synthesis and Biological Activity of Novel Neuroprotective Diketopiperazines, Bioorganic & Medicinal Chemistry, Sep. 2002, vol. 10, No. 9, pp. 3043-3048.

McCleland et al., An investigation into the biological activity of the selected histidine-containing diketopieperazines cyclo(His-Phe) and cyclo(His-Tyr), Journal of Pharmacy and Pharmacology, Sep. 2004, vol. 56, No. 9, pp. 1143-1153.

Weng et al., "Novel CCK-B receptor agonists: diketopiperazine analogues derived for CCK4 bioactive conformation" Regul Pept, Aug. 27, 1996; vol. 65(1): Abstract only.

Battersby et al., "Diketopiperazine formation and N-terminal degradation in recombinnat human growth hormone", Int J Pept Protein Res., Sep. 1994; vol. 44(3); Abstract only.

Lee et al., "Cyclo (Leu-Gly attenuates the striatal dopaminergic supersensitivity induced by chronic morphine.", Alcohol Drugs Res.; 1987; vol. 7(1): Abstract only.

Bressan et al. "Coordination chemistry of peptides. Part II. Crystal structure of cyclo-L-methionylglycine and studies of metal complexation", Int J Pept Protein Res; Apr. 1982; vol. 19(4); Abstract only.

Suzuki et al., "Effect of cyclic dipeptides containing histidine on pentobarbital narcosis", J Pharmacobiodyn; May 1981; vol. 4(5): Abstract only.

Jara et al., Elevated serum levels of cyclo (His-Pro), and endogenous inhibitor ofpituitary prolactin secretion, in systemic lupus erythematosus patients.:, Lupus; 1997; vol. 6(3); Abstract only.

Woehlecke et al., "Reversal of breast cancer resistance protein-mediated drug resistance by tryprostatin A.", Int J Cancer; Dec. 10, 2003; vol. 107(5); Abstract only.

"Tryprostatin A, *Aspergillus fumigatus*"; available at http://www.emdbiosciences.com/Products/ProductDisplay.asp?catno=649305&; printed on Jun. 21, 2006, 1 page.

Caballero et al., "Brief total systhesis of the cell cycle inhibitor tryprostatin B and related preparation of its alanine analogue.", J Org Chem.; Sep. 5, 2003; vol. 68(18); Abstract only.

Caballero et al., "Brief systhesis of the cell cycle inhibitor tryprostatin B and its alanine analogue.", Fourth International Electronic conference of Synthetic Organic Chemistry (ECXOC-4), Sep. 1-13, 2000, 4 pages, available at http://pages.unibas.ch/mdpi/eecxoc-4/c0023.htm.

Goolcharran et al. "Comparison of the rates of deamidation, diketopiperazine formation and oxidation in recombinant human vascular endothelial growth factor and model peptides." AAPS PharmSci., 2000; vol. 2(1); Abstract only.

Houston et al., "The cyclic dipeptide Cl-4 [cyclo-(l-Arg-d-Pro)] inhibits family 18 chitinases by structural mimicry of a reaction intermediate.", Biochem J.; Nov. 15, 2002; vol. 368(Pt 1); Abstract only.

Jamie et al., "The effect of the isomers of cyclo(Trp-Pro) on heart and ion-channel activity." J Pharm Pharmacol; Dec. 2002; vol. 54(12); Abstract only.

Strom et al., "*Lactobacillus plantarum* MiLAB 393 produces the antifungal cyclic dipeptides cyclo(L-Phe-L-Pro) and cyclo(L-Phe-trans-4-OH-L-Pro) and 3-phenyllactic acid.", Appl Environ Microbiol; Sep. 2002; vol. 68(9); Abstract only.

Serdenin et al. "Endogenous dipeptide cycloprolylglycine shows selective anxiolytic activity in animals with manifest fear reaction", Bull Exp Biol Med; Apr. 2002; vol. 1333(4); Abstract only.

Ostrovskaia et al., "Multicomponent antithrombotic effect of the neuroprotective prolyl dipeptide GVS-111 and its major metabolite cyclo-L-prolylglycine", Eksp Klin Farmakol; Mar.-Apr. 2002; vol. 65(2); Abstract only.

Fdhila et al., "dd-diketopiperazines: antibiotics active against *Vibrio anguillarum* isolated form marine bacteria associated with cultures of Pecten maximus." J Nat Prod; Oct. 2003; vol. 66(10); Abstract only.

Moldavkin et al., "[Effect of the novel dipeptide nootropic agent noopept and its metabolite cyclo-L-prolylglycine on the transcallosal evoked potential in the rat brain]", Eksp Klin Farmakol; Mar.-Apr. 2002; vol. 65(2); Abstract only.

Gudasheva et al., "Anxiolytic activity of endogenous nootropic dipeptide cycloprolylglycine in elevated plus-maze test" Bull Exp Biol Med; May 2001; vol. 131(5); Abstract only.

Liu et al., "Hydroxyprolylserine derivatives JBP923 and JBP485 exhibit the antihepatitis activities after gastrointestinal absorption in rats." J Pharmacol Exp Ther; Aug. 2000; vol. 294(2); Abstract only.

Gudasheva et al. "Identification of a novel endogenous memory facilitating cyclic dipeptide cyclo-prolylglycine in rat brain" FEBS Lett; Aug. 5, 1996; vol. 391(1-2); Abstract only.

Lindner et al., "[Effects of cyclic adenosine-3',5'-monophosphate and cyclo(Lys-Pro).HCl neuronotrophic factors in tissue culture]", J Himforsch, 1987; vol. 28(3); Abstract only.

Sato et al., "Comparison of the antiociceptive effect between the cyclic dipeptide cyclo[Tyr(Et)-homoarginine] and the linear dipeptide Boc-Tyr(Et)-homoarginine-Ome in rats.", Jpn J Pharmacol; Jan. 1984; vol. 34(1); Abstract only.

Bhargava, "The effect of melanotrophin release inhibiting factor (MIF) and cyclo (Leu-Gly) on the tolerance to morphine-induced antinociception in the rat: a dose-response study", Br J Pharmacol, Apr. 1981; 72(4); Abstract only.

Rainbow et al., "Distribution, survival and biological effects in mice of a behaviorally active, enzymatically stable peptide: pharmacokinetics of cyclo(Leu-Gly) and puromycin-induced amnesia" Pharmacol Biochem Behav.; May 1979; vol. 10(5); Abstract only.

Cui et al., "Novel Mammalian Cell Cycle Inhibitors, Tryprostatins A, B and Other Diketopiperazines Produced by *Aspergillus fumigatus* II. Physico-chemical properties and Structures", The Journal Of Antibiotics, Jun. 1996, p. 534-540.

Graz et al. "Mechanism of a anti-fungal action of selected cyclic dipeptides", Pharmazie; Nov. 2001; vol. 56(11); p. 900-1.

Graz et al "Cyclic Dipeptides in the Induction of Maturation for Cancer Therapy", J. Pharm. Pharmacol. 2000; vol. 52; p. 75-82.

Degrassi et al., "Plant Growth-Promoting *Pseudomonas putida* WCS358 Produces and Secretes Four Cyclic Dipeptides: Cross-Talk with Quorum Sensing Bacterial Sensors", Current Microbiology; 2002; vol. 45; p. 250-254.

Holden et al. "Quorum-sensing cross talk: isolation and chemical characterization of cyclic dipeptides from *Pseudomonas aeruginosa* and other Gram-negative bacteria"; Molecular Microbiology; 1999; vol. 33(6); p. 1254-1266.

Wretlind "The Availability of the Isopropyl Ester of L- and D-Phenylalanine and 3,6-Dibenzyl-2,5-Diketopiperazine form Growth in Rats", Acta phys. Scandinav, May 26, 1953, vol. 30, p. 97-104.

Walter et al., "The Cyclized C-Terminal Dipeptide of Arginine Vasopressin: Metabolic Stability and Antagonism of Puromycin-Induced Amnesia", Hormones and Behavior, 1982; vol. 16; p. 234-244.

Mizuma et al., "Intestinal Absorption of Stable Cyclic Glycylphenylalanine: Comparison with the Linear Form", J. Pharm. Pharmacol.; 1997; vol. 49; p. 1067-1071.

Hlinak et al., "Effect of alaptide, its analogues and oxiracetam on memory for an elevated plus-maze in mice", European Journal of Pharmacology; 1996; vol. 314, p. 1-7.

Mizuma et al., "Concentration-Dependent Preferences of Absorptive and Excretive Transport Cause Atypical Intestinal Absorption of Cyclic Phenylalanylserine: Small Intestine Acts as an Interface Between the Body and Ingested Compounds", Research Communications in Molecular Pathology and Pharmacology, 2002, vol. 111, p. 199-209.

Wang et al. Tetrahedron Letters 43:865-67 (2002).

Akiyama et al., Neurobiol. Aging (2000), 21, pp. 383-421.

Alvarez et al., "Isolation and Structure Elucidation of Two New Calpain Inhibitors from Streptomyces Griseus"; J. Antibiotics, 47(11):1195-1201 (Nov. 1994).

Arbabi et al., "Priming Interleukin 8 Production: Role of Platelet-Activating Factor and p38"; Arch Surg., 134(12):1348-1353 (Dec. 1999); 15pgs.

Au et al., "Effect of PDE4 Inhibitors on Zymosan-Induced IL-8 Release From Human Neutrophils: Synergism with Prostanoids and Salbutamol"; Br. J. Pharmacol, 123:1260-1266 (1998).

Balk, "Lesson 24, vol. 12—ARDS: Pathophysiology of SIRS and MODS" www.chestnet.org/education/pccu/vol12/ lesson24.html, pp. 1-19, printed Jul. 20, 2000.

Barrow et al., WIN 64821. a New Competitive Antagonist to Substance P, Isolated from an *Aspergillus* Species: Structure Determination and Solution Conformation; J. Org. Chem., 58:6016-6021 (1993).

Binisti et al.; "Structure-Activity Relationships in Platelet Activating Factor"; J. Lipid Mediat. Cell Signal; (Jan. 1997); vol. 15(2); pp. 125-144 (Abstract).

Brauns, et al., Anticancer Research 24:1713-20 (2004).

Chan et al., "Site-Specific N-Terminal Auto-Degradation of Human Serum Albumin"; Eur. J. Biochem., 227:524-528 (1995).

Cytokines and Autoimmune Diseases, edited by Kuchroo, et al., 2002, Humana Press Inc., Totowa, NJ, pp. 3-23, 389-406.

Database WPI Section Ch, Week 199844 Derwent Publications Ltd., London, GB; Class B03, AN 1998-515050 XP002369751.

Davidson et al. "Autoimmune Diseases", N. Engl. J. Med (2001) 345(5), pp. 340-350.

Dirr, K. et al: "The transformation of arginine into citrulline" Z. Physiol. Chem. , 237, 121-30, 1935.

Faden et al., J. Cerebral Blood Flow & Metabolism 23:355-63 (2003).

Faden, et al., J. Alzheimer's Dis. 6:S93-S97 (2004).

Faden, et al., J. Cerebral Blood Flow & Metabolism 23:342-54 (2003).

Gross et al., Regulation of Interleukin-8 Production in a Human Colon Epithelial Cell Line (HT-29); Gastroenterology, 108:653-661 (1995).

Hayashi et al., "Synthetic Hexa- and Heptapeptides That Inhibit IL-8 from Binding to and Activating Human Blood Neutrophils1"; J. Immunol., 154:814-824 (1995).

Ishii, et al. Toxicology Letters, 7:433-37 (1981).

Jackson I M D et al: "Amyotrophic Lateral Sclerosis TRH and Histidylproline Diketopiperazine in the Spinal Cord and Cerebrospinal Fluid" Neurology, vol. 36, No. 9, 1986, pp. 1218-1223, XP008090473 ISSN: 0028-3878.

Kaakkola Seppo; Wurtman Richard J: "Effects of two diketopiperazines, cyclo (His-Pro) and cyclo (Asp-Phe), on striatal dopamine: A microdialysis study" Brain Research Bulletin, vol. 32, No. 6, 1993, pp. 667-672, XP002369690.

Kulikov et al., "Review: The Bioregulatory Role of Platelet-Activating Factor ni Intracellular Processes and Cell—Cell Interactions", www.protein.bio.msu.su/biokhimiya/contents/v63/full/63010057.html, pp. 1-13 (1997).

McCain, et al. Int. J. Immunopharmoc. 8(4):443-46 (1986).

McCain, et al., Life Science, 41:169-76 (1987).

MeSH, "Autoimmune Diseases", internet document <<http://www.ncbi.nlm.nih.gov/sites/entrez>>, accessed Oct. 31, 2007, 2 pages.

Miller et al., "Peptide Inhibitor of Interleukin-8 (IL-8) Reduces Staphylococcal Enterotoxin-A (SEA) Induced Neutrophil Trafficking to the Lung" ; Inflamm. Res., 45:393-397 (1996).

Milne, et al. J. Pharm. Pharmacol., 50:1331-37 (1998).

Nitecki et al., J. Org. Chem., 33(2):864-866 (1968).

Palacios et al., "Tenidap Decreases IL-8 and Monocyte Chemotactic Peptide-1 (MCP-1) mRNA Expression in the Synovial Tissue of Rabbits with Antigen Arthritis and in Cultured Synovial Cells"; Clin. Exp. Immunol., 111:588-596 (1998).

Prasad C et al: "Increased cerebrospinal fluid cyclo(His-Pro) content in schizophrenia." Neuropeptides Nov. 1991, vol. 20, No. 3, Nov. 1991, pp. 187-190, XP002477203 ISSN: 0143-4179.

Purves et al., Life: the Science of Biology, 3rd Ed. (1992), p. 376.

Rainger et al., "Endothelial-Borne Platelet-Activating Factor and Interleukin-8 Rapidly Immobilize Rolling Neutrophils"; Am. J. Physiol., 272(Heart Circ. Physiol. 41):H114-H122 (1997).

Rainsford et al., "Effects of 5-Lipoxygenase Inhibitors on Interleukin Production by Human Synovial Tissues in Organ Culture: Comparison with Interleukin-1-Synthesis Inhibitors"; J. Pharm. Pharmacol., 48:46-52 (1996).

Roth et al., "Platelet-Activating Factor Exerts Mitogenic Activity and Stimulates Expression of Interleukin 6 and Interleukin 8 in Human Lung Fibroblasts via Binding to its Functional Receptor"; J. Exp. Med., 184:191-201 (1996).

Sakurada et al. J. Pharm. Pharmacol., 34:750-51 (1982).

Sakuta et al., "Dual Regulatory Effects of Interferon-$\alpha$, -$\beta$, and -$\gamma$ on Interleukin-8 Gene Expression by Human Gingival Fibroblasts in Culture Upon Stimulation with Lipopolysaccharide from Prevotella Intermedia, Interleukin-1$\alpha$, or Tumor Necrosis Factor-$\alpha$"; J. Dent Res., 77(8):1597-1605 (1998).

Sano et al. "Process Research and Developmment of L-Alanyl-L-Glutamine, a Component of Parenteral Nutrition", Organic Process Research & Development, 2000, vol. 4, pp. 147-152.

Shimazaki et al., "Diketopiperazine Derivatives, a New Series of Platelet-Activating Factor Inhibitors"; Chem. Pharm. Bull., 35(8):3527-3530 (1987).

Shimazaki et al., "Diketopiperazines as a New Class of Platelet-Activating Factor Inhibitors"; J. Med. Chem., 30:1706-1709 (1987).

Shimazaki et al., "PAF Inhibitory Activity of Diketopiperazines: Structure-Activity Relationships"; Lipids, 26(12):1175-1178 (1991).

Smith et al., "Lesson 10, vol. 12—Asthma: Evolving Anti-Inflammatory Therapy", www.chestnet.org/education/pccu/vol12/lesson10.html, pp. 1-8, printed Jul. 20, 2000.

Smith et al., Bioorg. Med. Chem., 8:2369-2374 (1998).

Smith et al., Darlington. Mult. Scler. (1999) 5, pp. 110-120.

t'Hart et al., DDT (2004) 9(12), p. 517-524.

The Cytokine Handbook, editied by Thomson and Lotze, 4th edition, 2003 Academic Press, vol. I, London, UK, pp. 167-199, 456-474, 567-601.

The Cytokine Handbook, editied by Thomson and Lotze, 4th edition, 2003 Academic Press, vol. II, London, UK, pp. 838-860 and 1189-1211.

Unal et al., Brain Research, 747(1):52-59 (1997).

Walter et al. Proc. Natl. Acad. Sci. 72: No. 10, pp. 4180-4184 (1975).

Yoshida et al., "PAF Inhibitors of Microbial Origin"; Prog. Biochem. Pharmacol., 22:68-80 (1988).

International Search Report for International (PCT) Patent Application No. PCT/US03/31226, mailed Jun. 14, 2005.

International Preliminary Examination Report for International (PCT) Patent Application No. PCT/US03/31226, mailed Nov. 29, 2005.

Examiner's First Report for Australian Patent Application No. 2003279761, mailed Jun. 16, 2008.

Supplementary Partial European Search Report for European Patent Application No. 03773099, mailed May 6, 2008.

Examination Report for New Zealand Patent Application No. 539735, mailed May 10, 2006.

Examination Report for New Zealand Patent Application No. 542886, mailed Nov. 28, 2007.

Examination Report for New Zealand Patent Application No. 539735, mailed Jan. 10, 2008.

Examination Report for New Zealand Patent Application No. 539735, mailed May 20, 2008.

Walter et al. Proc. Natl. Acad. Sci. 72, 4180-4184 (1975).

Examination Report for European Patent Application No. 03773099, mailed Feb. 4, 2009.

Sano et al. "Process Research and Development of L-Alanyl-L-Glutamine, a Component of Parenteral Nutrition", Organic Process Research & Development, 2000, vol. 4, pp. 147- 152.

Shimazaki et al., "Diketopiperazine Derivatives, a New Series of Platelet-Activating Factor Inhibitors"; Chem. Pharm. Bull., 35(8):3527-3530 (1987).

Shimazaki et al., "Diketopiperazines as a New Class of Platelet-Activating Factor Inhibitors"; J. Med. Chem., 30:1706-1709 (1987).

Shimazaki et al., "PAF Inhibitory Activity of Diketopiperazines: Structure-Activity Relationships"; Lipids, 26(12):1175-1178 (1991).

Smith et al., "Lesson 10, vol. 12—Asthma: Evolving Anti-Inflammatory Therapy", www.chestnet.org/education/pccu/vol12/lesson10.html, pp. 1-8, printed Jul. 20, 2000.

Smith et al., Bioorg. Med. Chem., 8:2369-2374 (1998).

Smith et al., Darlington. Mult. Scler. (1999) 5, pp. 110-120.

t'Hart et al., DDT (2004) 9(12), p. 517-524.

The Cytokine Handbook, editied by Thomson and Lotze, 4th edition, 2003 Academic Press, vol. I, London, UK, pp. 167-199, 456-474, 567-601.

The Cytokine Handbook, editied by Thomson and Lotze, 4th edition, 2003 Academic Press, vol. II, London, UK, pp. 838-860 and 1189-1211.

Unal et al., Brain Research, 747(1):52-59 (1997).

Walter et al. Proc. Natl. Acad. Sci. 72: No .10, pp. 4180-4184 (1975).

Yoshida et al., "PAF Inhibitors of Microbial Origin"; Prog. Biochem. Pharmacol., 22:68-80 (1988).

International Search Report for International (PCT) Patent Application No. PCT/US03/31226, mailed Jun. 14, 2005.

International Preliminary Examination Report for International (PCT) Patent Application No. PCT/US03/31226, mailed Nov. 29, 2005.

Examiner's First Report for Australian Patent Application No. 2003279761, mailed Jun. 16, 2008.

Supplementary Partial European Search Report for European Patent Application No. 03773099, mailed May 6, 2008.

Examination Report for New Zealand Patent Application No. 539735, mailed May 10, 2006.

\* cited by examiner

DIAGNOSIS OF MULTIPLE SCLEROSIS WITH DIKETOPIPERAZINES

CROSS-REFERENCE TO RELATED APPLICATIONS

This application claims the benefit of provisional applications 60/415,908, filed Oct. 2, 2002, 60/489,039, filed Jul. 21, 2003, and 60/503,185, filed Sep. 15, 2003. The complete disclosures of these three applications are incorporated herein by reference.

FIELD OF THE INVENTION

The invention relates to the diagnosis and monitoring of diseases and medical conditions by quantitating one or more biochemical markers associated with the diseases or conditions. In particular, the invention relates to the detection and measurement of diketopiperazines composed of the two N-terminal amino acids of disease-associated proteins, diketopiperazines composed of the two C-terminal amino acids of disease-associated proteins, truncated disease-associated proteins missing the two N-terminal amino acids and/or the two C-terminal amino acids, and other biochemical markers of such diseases and conditions.

BACKGROUND

Simpler and faster tests for diagnosing and monitoring diseases and medical conditions are always needed. In addition, many serious illnesses remain difficult to diagnose and monitor, and methods of diagnosing and monitoring these diseases and conditions are critically needed.

For instance, multiple sclerosis (MS) is difficult to diagnose because the progress, severity and specific symptoms of MS are quite variable and unpredictable. There are no laboratory tests, symptoms or physical findings that can, by themselves, determine if a person has MS.

The long established criteria for diagnosing MS are:

1. There must be objective evidence of two attacks (i.e., two episodes of demyelination in the central nervous system (CNS)). An attack (also known as an exacerbation, flare or relapse) is defined clinically as the sudden appearance or worsening of an MS symptom or symptoms, which lasts at least 24 hours. The objective evidence comes from findings of a neurological examination and additional tests.

2. The two attacks must be separated in time (at least one month apart) and space (indicated by evidence of inflammation and/or damage in different areas of the CNS).

3. There must be no other explanation for these attacks or the symptoms the person is experiencing. Many symptoms that are common in MS can also be caused by other diseases. Therefore, the MS diagnosis can only be made by carefully ruling out all possibilities.

Over the last twenty years, tests such as magnetic resonance imaging (MRI), examination of cerebrospinal fluid, and evoked response testing have played an increasingly important role in the diagnostic process. In 2001, the International Panel on the Diagnosis of Multiple Sclerosis issued a revised set of diagnostic criteria (*Annals of Neurology*, 50:121-127 (2001)). In addition to the traditional requirements given above, the revised criteria provide specific guidelines for using findings of MRI, cerebrospinal fluid analysis and visual evoked potentials to provide evidence of the second attack and thereby confirm the diagnosis more quickly. These guidelines also facilitate the diagnostic process in those patients who have had steady progression of disability without distinct attacks. However, even with these revised criteria, diagnosis of MS is still difficult and still typically takes several months or even years.

Due to the possibility of worsening or recurrence of MS, making a conclusive diagnosis quickly would be of great benefit. Drugs for the treatment of MS are now available which slow or prevent progression of the disease in many patients, and a quick diagnosis would allow early intervention and could significantly improve the prognosis for many MS patients.

The diagnosis of Alzheimer's disease is difficult and often relies on the exclusion of other causes. Various cognitive tests are employed to possibly identify the disease. However, a definitive diagnosis is only possible by a brain autopsy after death. Clearly, a diagnostic test that can provide a diagnosis for living Alzheimer's disease patients is needed.

Brain ischemia is currently a clinical diagnosis. Although certain biochemical markers have been described, such as Enolase, S-100 family of proteins and others, the imaging techniques available to the clinician are more reliable and specific. A reliable and specific biochemical marker for brain ischemia would be helpful in the diagnosis and monitoring of this disease.

Early cardiac ischemia is also difficult to diagnose. Cardiac markers of cellular necrosis, such as creatine kinase isoenzymes (CK-MB), myoglobin, or troponin, are unreliable markers of transient myocardial ischemia, particularly when measured in the first 2 to 6 hours after an ischemic event. Kontos, M. C. and R. L. Jesse, *Am J Cardiol*, 2000. 85(5A): p. 32B-39B; Ishikawa, Y., et al., *Clin Chem*, 1997. 43(3): p. 467-75; Brogan, G. X., Jr., et al., *Acad Emerg Med*, 1997. 4(1): p. 6-12; Hedges, J. R., et al., *Acad Emerg Med*, 1996. 3(1): p. 27-33. Patients who are examined soon after the onset of ischemic symptoms typically require prolonged observation to rule out myocardial infarction or myocardial ischemia. Gomez, M. A., et al., *J Am Coll Cardiol*, 1996. 28(1): p. 25-33; Zalenski, R. J., et al., *Arch Intern Med*, 1997. 157(10): p. 1085-91; de Winter, R. J., et al., *Ann Emerg Med*, 2000. 35(2): p. 113-20; Peacock, W. I., et al. *Ann Emerg Med*, 2000. 35(3): p. 213-20.

A novel blood assay method to measure reduced exogenous cobalt binding to human serum albumin in patients with myocardial ischemia has been described. Bar-Or et al., *J. Emerg. Med.*, 2000. 19(4): p. 311-5. The albumin-cobalt binding (ACB) assay measures the binding capacity of exogenous cobalt to the amino terminus (N-terminus) of human albumin. Under normal conditions, transition metals, including cobalt,. are tightly bound to the exposed N-terminus of albumin. Kubal, G., P. J. Sadler, and A. Tucker, *Eur J Biochem*, 1994. 220(3): p. 781-7. The ACB assay is based on observations that ischemic conditions may alter the N-terminus of albumin and rapidly reduce its binding capacity for transition metals. Berenshtein et al., *J. Mol. Cell. Cardiol.*, 1997. 29(11): p. 3025-34; Bar-Or et al., *Eur. J. Biochem.*, 2001. 268(1): p. 42-47. Ischemia-induced alterations to albumin would be predicted to occur minutes or hours before abnormal levels of CK-MB, myoglobin, or troponin could be detected. However, the ACB assay has been approved only as a test to rule out cardiac ischemia, and it would be highly desirable to have an assay that could diagnose cardiac ischemia, as well as rule it out.

Low birth weight (LBW) is the leading cause of fetal and neonatal morbidity and mortality worldwide. LBW is generally accepted to indicate a weight of less than 2500 grams at delivery, and may result from a newborn being born at term but small for gestational age (SGA), being born preterm and appropriate for gestational age (AGA) or being both preterm and SGA. As such, the epidemiology of LBW is complex and multifactorial.

SGA is a statistical definition, indicating that the birth weight is less than the tenth percentile for gestational age. By definition then, 10% of newborns are SGA. In practice, some of these newborns are small and well, fulfilling their genetic growth potential, and are not at substantial risk. Other SGA newborns on the other hand are truly growth impaired, failing to meet their genetic growth potential due to a variety of factors as discussed below. These newborns are said to suffer from fetal growth restriction (FGR). In practice, some infants are presumably AGA and suffer from FGR; that is to say their weight may be at the $20^{th}$ percentile for gestational age, but they were genetically programmed to weigh at the $80^{th}$ percentile. These infants are difficult to identify in a practical sense, as there is no a priori way of knowing how much an individual "should" weigh.

FGR leads to LBW both by direct impairment of fetal growth, and often in addition by necessitating indicated preterm delivery due to compromised fetal status or associated maternal disease (e.g., preeclampsia). Morbidity due to LBW and/or prematurity is varied and substantial and well documented elsewhere. Additionally, recent data have suggested that a compromised intrauterine environment can have a profound influence on health in adult life, the so-called "fetal origins of disease" or Barker hypothesis. Via these various mechanisms, the disease burden attributable to FGR is tremendous.

While the fetus/neonate is often the focus of concern in pregnancies complicated by FGR, it is important to recall that these pregnancies are also often complicated by conditions that directly threaten maternal health. Most notably, preeclampsia, whose precise pathophysiology remains obscure, has long been felt to result from placental ischemia. Preeclampsia and its complications are the leading causes of maternal mortality worldwide.

While the differential diagnosis of FGR is diverse, including chromosomal, toxic, viral and other etiologies, the majority of cases result from uteroplacental insufficiency (UPI). UPI may be associated with a variety of maternal diseases (hypertension, renal disease, systemic lupus erythematosus, antiphospholipid syndrome, thrombophilia, etc.), pregnancy complications (placental abruption, preeclampsia), or may be idiopathic. Regardless of the etiology, the presumed unifying underlying pathophysiology results from reduced placental blood flow (ischemia) in either the maternal or the fetal circulation, or both.

As a crude measure, it is known that there is a direct relationship between placental weight and fetal weight, suggesting that placental resources might control fetal growth to some extent. There are a large number of placental pathologic lesions associated with FGR. In general, these are lesions that would be expected to compromise maternal and/or fetal blood flow. The association between reduced maternal and/or fetal blood flow (ischemia) and FGR is also corroborated by a large amount of Doppler flow data in affected pregnancies. In many cases, these abnormal Doppler flow waveforms correlate well with abnormal placental pathology.

While much is known about the pathophysiology of FGR, much remains to be understood. In the clinical setting, although various risk factors for FGR are recognized, their positive predictive values and sensitivities are limited. There can be difficulty differentiating the FGR fetus from the "SGA but well" fetus. Recognizing this difference is important to avoid unnecessary interventions on well pregnancies. Early identification of pregnancies destined to be affected by FGR might help foster appropriate follow-up. Timing of delivery is also a matter of intense interest, balancing the benefits of advancing gestation against those of continuing in an ischemic environment. Finally, on a more fundamental level, access to a clinical test to identify placental ischemia and quantify its severity might ultimately help foster appropriate treatment or even prevention.

As noted above, the ACB assay for ruling out ischemia is based on observations that ischemic conditions may alter the N-terminus of human serum albumin and rapidly reduce its binding capacity for transition metals. The nature of the alterations of the N-terminus of human serum albumin that may account for its reduced metal binding capacity have not been identified, but cleavage of 1-4 amino acids has been proposed as one of several possibilities. See PCT application WO 00/20840. In particular, it has been hypothesized that cleavage of the N-terminal dipeptide (Asp-Ala or DA) from human serum albumin and the cyclization of the dipeptide to form the diketopiperazine (DA-DKP) may partially explain the observation of reduced metal binding to N-terminus of human serum albumin in ischemia. Bar-Or et al., *Biochem. Biophys. Res. Commun.*, 84:856-862 (Jun. 15, 2001). However, this article does not teach or suggest that DA-DKP can be used as a marker of ischemia.

PCT application WO 00/20454 discloses a marker for free radical damage. The marker is human serum albumin whose N-terminal metal binding site has been modified by free radical damage. Reduced metal binding to the altered N-terminus is used to detect and measure the free radical damage. Several possible modifications of the N-terminus of human serum albumin that might account for the reduced metal binding are proposed, including the possibility that the N-terminal dipeptide (DA) is cleaved by free radicals and that this dipeptide then cyclizes to form DA-DKP. Although direct detection of the altered N-terminus of human serum albumin is suggested as a method of detecting and measuring free radical damage, measurement of the hypothetical DA-DKP is not taught or suggested for this purpose.

Elevated levels of histidine-proline diketopiperazine (HP-DKP) have been detected in neurological disorders, including non-medicated schizophrenics and patients suffering from amyotrophic lateral sclerosis (Prasad, *Peptides*, 1995 16:1 pp. 151-164), and in patients with renal failure (Takahara et al., *J. Clinical Endocrinol. Metab.* 1983 56:2 pp. 312-319). HP-DKP may be derived from thyrotropin-releasing hormone (TRH) or its precursor (preproTRH) by unknown mechanisms and/or from other sources (Prasad, *Peptides*, 1995 16:1 pp. 151-164).

SUMMARY OF THE INVENTION

The present invention is based on the discovery of objective biochemical markers useful for diagnosing and monitoring various diseases and medical conditions. The markers include diketopiperazines composed of the two N-terminal amino acids or the two C-terminal amino acids of disease-associated proteins. The term "protein" is used herein to mean protein, polypeptide, oligopeptide or peptide, and the term "disease-associated proteins" is used herein to mean proteins associated with specific diseases or conditions, including proteins from organs or tissues ("organ-specific" or "tissue-specific" proteins) affected by a disease or condition. The markers also include truncated disease-associated proteins from which the two N-terminal amino acids and/or the two C-terminal amino acids are missing. These markers are collectively referred to herein as "target markers".

Accordingly, the present invention provides a method of diagnosing or monitoring a disease or condition comprising determining the quantity of one or more target markers in a biological sample and determining if the quantity(ies) of the marker(s) is(are) indicative of the presence, absence or status of the disease or condition. The target markers can be measured rapidly and conveniently, and these measurements provide objective evidence which will allow a reliable diagnosis to be made easily and quickly for diseases and conditions, such as, for example, multiple sclerosis, Alzheimer's disease and ischemia, particularly placental ischemia. This method will be of great benefit, since it will allow treatment of many diseases and conditions to begin much earlier than is now possible. In addition, the measurement of the target markers will allow the status of the diseases or conditions to be monitored, allowing for more effective treatment of many diseases, conditions and disorders and for the evaluation of new drugs and other treatments.

The present invention further provides methods of diagnosing or monitoring multiple sclerosis (MS) using a MS diagnostic compound. The methods comprise obtaining a biological sample from a patient to be tested and measuring the amount of one or more MS diagnostic compounds in the biological sample. MS diagnostic compounds include: (i) a compound having a mass of about 175 as determined by liquid chromatography and mass spectrometry (LC-MS); (ii) a compound having a mass of about 145 as determined by LC-MS; (iii) Asp-Ala diketopiperazine (DA-DKP); and (iv) N-acetyl-alanine-serine diketopiperazine (NAS-DKP). The absence of compounds (i) and/or (ii) or an elevated level of DA-DKP and/or NAS-DKP in the biological sample is indicative of MS. Also, an elevated level of DA-DKP and/or NAS-DKP in the biological sample is indicative of active MS. Other MS diagnostic compounds are listed in Tables 1 and 2.

In a further embodiment, the invention provides methods of diagnosing or monitoring Alzheimer's disease using various markers of the disease. In particular, the methods comprise obtaining a biological sample from a patient to be diagnosed or monitored and measuring the amount of one or more Alzheimer's diagnostic compounds in the biological sample. Alzheimer's diagnostic compounds include: (i) a compound having a mass of about 175 as determined by liquid chromatography and mass spectrometry; and (ii) DA-DKP. Both Alzheimer's diagnostic compounds have been found elevated in the plasma of Alzheimer's patients. Other Alzheimer's diagnostic compounds are listed in Tables 1 and 2.

In yet another embodiment, the invention provides methods of diagnosing or monitoring placental ischemia in pregnant patients. The methods comprise obtaining a biological sample from a pregnant patient and measuring the amount of one or more placental ischemia diagnostic compounds in the biological sample. Placental ischemia diagnostic compounds include Gly-Leu diketopiperazine (GL-DKP) and Ala-Pro diketopiperazine (AP-DKP). Other placental ischemia diagnostic compounds are listed in Tables 1 and 2.

The invention also provides novel binding partners having specificity for the diketopiperazines. The binding partners are preferably antibodies and/or aptamers that specifically recognize the diketopiperazines of the present invention. Such binding partners can be used in the methods of the present invention. Compositions and kits containing the novel binding partners are also provided.

DETAILED DESCRIPTION OF THE PRESENTLY PREFERRED EMBODIMENTS OF THE INVENTION

Figure 1:
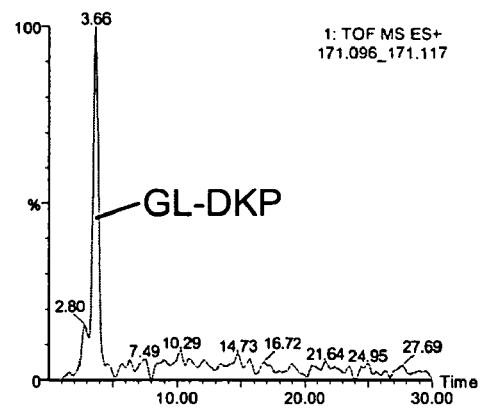
FIG. 1: Printout from a mass spectrometer. The sample was recombinant beta-human chorionic gonadotropin processed by liquid chromatography followed by mass spectrometry.

The invention generally provides methods of diagnosing and monitoring diseases, conditions and disorders by quantitating markers for the diseases and conditions.

In one embodiment, the present invention provides methods of diagnosing and monitoring diseases or conditions characterized by the degradation of disease-associated proteins. The degradation products include diketopiperazines composed of the two N-terminal amino acids or the two C-terminal amino acids and the corresponding truncated disease-associated proteins lacking such terminal amino acids. Accordingly, the present invention is based on the discovery that these degradation products are useful markers for diagnosing and monitoring diseases, conditions and disorders.

As noted above, the term "disease-associated proteins" is used herein to mean proteins associated with specific diseases, conditions or disorders, including proteins from organs or tissues ("organ-specific" or "tissue-specific" proteins) affected by a disease, condition or disorder. Examples of disease-associated proteins and their corresponding diseases and conditions are listed in Tables 1 and 2. Those skilled in the art can readily determine, without undue experimentation, other disease-associated proteins, their corresponding diseases or conditions, and useful markers based on the guidance provided herein.

The target markers quantified in the methods of this embodiment are formed by the degradation of the disease-associated proteins. It is believed that this degradation occurs in diseases or conditions involving or caused by acidosis, reactive oxygen species (ROS), inflammation, and/or conditions which cause the protonation of the N-terminal or C-terminal amino acids of the disease-associated proteins, such as the binding of certain ligands to the N-terminal or C-terminal amino acid. Diketopiperazines can also be formed in vivo due to the action of certain enzymes (e.g., dipeptidyl peptidases or carboxypeptidases), and the activity of these enzymes may be altered in certain diseases, conditions and disorders. Dipeptidyl peptidases are amino peptidases which cleave the two amino acids of the N-termini of proteins with some specificity, while carboxypeptidases cleave amino acids from the C-termini of proteins. The placenta, for example, is rich in dipeptidyl peptidase IV. After the cleavage, or under specific conditions, the enzymes may be responsible for cyclization, as well as cleavage, of the amino acids. Alternatively, the second step (cyclization) may be non-enzymatic and may require the protonation of the N-terminus or C-terminus. Thus, the markers useful in the present invention include diketopiperazines composed of two amino acids from either terminal end of a disease-associated protein and the truncated disease-associated proteins without the two N-terminal and/ or the two C-terminal amino acids.

As used herein, "X-Y DKP" or "X-Y-DKP" means a diketopiperazine (cyclic dipeptide) composed of two amino acids, X and Y, wherein X and Y are the two N-terminal or the two C-terminal amino acids of a disease-associated protein. X and Y may be the same or different and each may be any amino acid, including any post-translationally modified amino acid. Notwithstanding the foregoing, X-Y DKP may not be His-Pro DKP when a single diketopiperazine is the only marker measured. Table 3 lists the conventional three-letter and single-letter abbreviations for each amino acid. Post-translational modifications of amino acids are well known and include phosphorylation, acylation, cysteinylation, nitrosylation, and glycosylation.

Examples of diketopiperazines useful as markers in the present invention are listed in Tables 1 and 2 along with their corresponding diseases and disease-associated proteins. Those skilled in the art can readily identify, without undue experimentation, other diketopiperazines derived from the two N-terminus amino acids or the two C-terminus amino acids of a disease-associated protein that can be used as target markers of various diseases and conditions.

TABLE 1

| Disease | Protein | N-terminal DKP | MW |
|---|---|---|---|
| Multiple Sclerosis | Myelin basic protein (MBP) | N-acetyl-Ala-phospho-Ser | 280 |
|  | MBP | N-acetyl-Ala-Ser | 200 |
|  | Beta-amyloid | Asp-Ala | 186 |
| Rheumatoid Arthritis | Rh Factor | Glu-Ile | 242.3 |
| ARDS*, | Pulmonary | (A) Glu-Val | 228.24 |
| Cystic Fibrosis | surfactant-associated proteins A, B and D | (B) Phe-Pro (D) Ala-Glu |  |
| Diabetes Mellitus | Insulin | Phe-Val | 246.34 |
|  |  | Gly-Ile | 170.24 |
| Alzheimer's disease | Beta-amyloid tau protein | Asp-Ala Met-Ala | 186.15 |
| Parkinson's disease | alpha-synuclein | Met-Asp | 246.31 |
|  |  | Glu-Lys | 257.38 |
| Inflammation (general)** | Albumin | Asp-Ala | 186.15 |
|  | C-reactive protein | Gln-Thr | 229.23 |
|  | Interleukin 8 | Ala-Val | 170.2 |
| Ischemia (general) | Albumin | Asp-Ala | 186.15 |
| Cerebral Ischemia | S100 family of proteins | Many | Many |
| Placental Ischemia | Beta-chorionic gonadotropin | Gly-Leu | 170.24 |
|  | Fetal erythropoietin | Ala-Pro | 168.18 |
|  | Pregnancy-associated protein A | Glu-Ala |  |
| Myocardial Infarction | Myoglobin | Gly-Leu | 170.24 |
|  | Troponin I | Pro-Glu | 226.22 |
| Prostate Cancer | Prostate Specific Antigen (PSA) | Lys-Ser Ile-Val | 215.28 |
| Pancreatitis | Amylase | Gln-Tyr | 291.3 |
|  | Lipase | Lys-Glu | 257.28 |
| Emphysema | alpha1-antitrypsyn | Glu-Asp | 244.23 |
| Renal Disease, Cancer, Chemotherapy | Erythropoietin | Ala-Pro | 168.18 |
| Sepsis | Activated protein C | Ala-Asn | 185.17 |
| Hemoglobinopathies, Amemias | Tethal Chain | Ala-Leu | 199.24 |
|  | Zeta Chain | Ser-Leu | 215.24 |
|  | Alpha Chain | Val-Leu | 227.3 |
|  | Beta Chain | Val-His | 236.27 |
|  | Delta Chain | Val-His | 236.27 |
|  | Epsilon Chain | Val-His | 236.27 |
|  | Gamma AG | Gly-His | 194.19 |

TABLE 1-continued

| Disease | Protein | N-terminal DKP | MW |
|---|---|---|---|
| Congestive heart failure | Brain natriuretic peptide | His-Pro Ser-Pro | 234.25 184.18 |

TABLE 2

| Disease | Protein | C-terminal DKP | MW |
|---|---|---|---|
| Multiple Sclerosis | Myelin basic protein (MBP) | Arg—Arg | 312.36 |
|  | Beta-amyloid | Gln-Asn | 242.23 |
| Rheumatoid Arthritis | Rh Factor | Lys-Arg | 284.35 |
| ARDS*, | Pulmonary | (A) Glu-Phe | 276.28 |
| Cystic Fibrosis | surfactant-associated proteins A, B and D | (B) Ser-Met (D) Glu-Phe | 218.26 276.28 |
| Diabetes Mellitus | Insulin | Cys-Asn | 217.24 |
|  |  | Lys-Ala | 199.24 |
| Alzheimer's disease | Beta-amyloid tau protein | Gln-Asn Gly-Leu | 242.23 170.21 |
| Parkinson's disease | alpha-synuclein | Ala—Ala Ala—Ala | 142.14 142.14 |
| Inflammation (general)** | Albumin | Gly-Leu | 170.21 |
|  | C-reactive protein | Trp-Pro | 283.32 |
|  | Interleukin 8 | Asn-Ser | 201.17 |
| Ischemia (general) | Albumin | Gly-Leu | 170.21 |
| Cerebral Ischemia | S100 family of proteins | Many | Many |
| Placental Ischemia | Beta-chorionic gonadotropin | Leu-Pro | 210.27 |
|  | Fetal erythropoietin | Asp-Arg | 271.26 |
|  | Pregnancy-associated protein A | His-Gly | 194.19 |
| Myocardial Infarction | Myoglobin | Gln-Gly | 185.18 |
|  | Troponin I | Glu-Ser | 216.18 |
| Prostate Cancer | Prostate Specific Antigen (PSA) | Asn-Pro Asn-Pro | 211.21 211.21 |
| Pancreatitis | Amylase | Lys-Leu | 241.33 |
|  | Lipase | Pro-Cys | 200.25 |
| Emphysema | alpha1-antitrypsyn | Asn-Lys | 256.3 |
| Renal Disease, Cancer, Chemotherapy | Erythropoietin | Asp-Arg | 271.26 |
| Sepsis | Activated protein C | Ala-Pro | 168.18 |
| Hemoglobinopathies, Amemias | Tethal Chain Zeta Chain Alpha Chain Beta Chain Delta Chain Epsilon Chain Gamma AG |  |  |
| Congestive heart failure | Brain natriuretic peptide | Arg-His | 293.32 |

*ARDS = acute respiratory distress syndrome.
**Asp-Ala diketopiperazine (DA-DKP) and/or Gly-Leu diketopiperazine (GL-DKP) derived from albumin, a circulating protein, will be general markers of inflammation. Other diketopiperazines derived from disease-associated proteins, including those found in specific organs or tissues, will be markers of inflammation in those organs and tissues or associated with those diseases and conditions.

TABLE 3

| Amino Acid | Three-Letter abbreviation | Single-Letter abbreviation |
| --- | --- | --- |
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Gluatmine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Other useful target markers formed by the degradation of the disease-associated protein are referred to as "truncated disease-associated proteins." As noted previously, these truncated disease-associated proteins lack the two N-terminal amino acids and/or the two C-terminal amino acids and, therefore, can be utilized as target markers in the present methods. However, the truncated disease-associated protein may not be human serum albumin lacking the two N-terminal amino acids. Truncated disease-associated proteins include, for example, myelin basic protein missing the amino acids N-acetyl-Ala and Ser from the N-terminus and beta-amyloid missing the amino acids Asp and Ala from the N-terminus, both of which are useful target markers of multiple sclerosis. Truncated beta-amyloid missing the two N-terminal amino acids Asp and Ala and truncated tau protein missing the two C-terminal amino acids Gly and Leu are examples of target markers for Alzheimer's disease. Those skilled in the art can readily identify other useful truncated disease-associated proteins as target markers of various diseases and conditions.

In the first embodiment of the present invention, the methods comprise:

(a) obtaining a biological sample from a patient to be diagnosed or monitored;

(b) determining the quantity of one or more target markers of the disease or condition; and (c) determining if the quantity(ies) of the target marker(s) is(are) indicative of the presence, absence or status of the disease or condition.

In the methods, the target markers can be quantified in any suitable biological sample derived from the patient to be diagnosed or monitored. Biological samples include suitable body fluids, such as serum, plasma, blood, urine, saliva, cerebrospinal fluid, tears, semen, vaginal secretions, amniotic fluid and cord blood. Also, lavages, tissue homogenates and cell lysates can be utilized and, as used herein, biological samples include such preparations.

The biological samples can be taken from a patient. The term "patient" includes any animal, preferably mammals, and most preferably humans. Those skilled in the art can readily determine appropriate diseases or conditions and their corresponding target markers for a particular patient.

The quantity of the target marker can be measured by any means known to those skilled in the art, including, for example, by mass spectrometry, immunoassays, chemical assays, sensitive liquid chromatography without mass spectrometry, and a variety of direct and indirect photometric techniques. For instance, a variety of analytical methods can be used to quantitate the target marker by mass spectrometry. Generally, the marker of interest can be isolated from the biological sample by a suitable technique, such as liquid chromatography or two-dimensional gel electrophoresis. Then the target marker can be quantitated by any mass spectrometry detection method, such as electrospray ionization mass spectrometry, liquid chromatography tandem mass spectrometry (LC-MS), matrix-assisted laser desorption/ionization mass spectrometry (MALDI-MS), MALDI time-of-flight MS (MALDI-TOF-MS), etc. See, e.g., Lim et al., *Analytical Biochemistry*, 295: 45-56 (2001). The target markers can be quantitated using pure marker standards of known quantity or by comparison to the same target markers in the same type of biological samples from normal controls.

Immunoassays are preferably used to quantitate the target markers. Immunoassays employ one or more binding partners. A "binding partner" is any compound or molecule capable of specifically binding to a target marker. As used herein, "specifically" means the binding partner binds to the target marker selectively in the presence of other compounds. Binding partners are preferably antibodies, aptamers, lectins and other molecules that can specifically bind to the target marker. Such binding partners can be used separately or in combination (e.g., antibodies can be used in combination with aptamers). Suitable binding partners are described below as a further embodiment of the present invention.

Those skilled in the art can readily determine immunoassay formats suitable for use in the methods of the present invention. Such immunoassays include homogeneous assays, heterogeneous assays, enzyme immunoassays (e.g., ELISA), competitive assays, immunometric (sandwich) assays, turbidimetric assays, nephelometric assays, and the like. The immunoassays can be performed manually or with an automated analyzer.

In a preferred enzyme immunoassay, a binding partner specific for the target marker is immobilized on a solid substrate. Suitable solid substrates are well known and include, for example, glass, polystyrene, polypropylene, polyethylene, nylon, polyacrylamide and agarose. The biological sample is contacted with the immobilized binding partner. After washing, the target marker bound to the solid substrate by the bound binding partner is reacted with a second binding partner (e.g. a second antibody or a mixture of antibodies) specific for a known epitope on the target marker. The second binding partner can be labeled to quantitate the target marker or a labeled third binding partner or other compound (e.g., protein A or streptavidin) can be used to quantitate the marker.

As an alternative, the target marker can first be separated from the other constituents of the biological sample by, e.g., affinity chromatography. For affinity chromatography, antibodies specific for the target marker are attached to a solid surface (e.g., beads in a column) and used to bind the target marker in the sample. After washing the solid surface, the target markers are eluted and measured (e.g., by one of the methods described above, by measuring the absorbance at 280 nm or by any another method known to those skilled in the art).

Suitable labels for any of the binding partners (e.g. primary, secondary or third antibody) are well known in the art. Such labels include: (i) enzymes (e.g., horseradish peroxidase, malate dehydrogenase, staphylococcal nuclease, delta- 5-steriod isomerase, yeast alcohol dehydrogenase, alphaglycerophosphate dehydrogenase, triose phosphate isomerase, alkaline phosphatase, asparaginase, glucose oxidase, betagalatosidase, ribonuclease, urease, catalase, glucose-6-phosphate dehydrogenase, glucoamylase and acetylcholine esterase); (ii) fluorophores (e.g., fluorescein isothiocyanate, rhodamine, phycoerythrin, phycocyanin, allophycocyanin, o-phtaldehyde and fluorescamine); (iii) radionucleotides (e.g., indium-111, technetium-99m, iodine-125, gallium-67 and gallium-68); (iv) bioluminescent labels (e.g., luciferin, luciferase and aequorin); (v) chemiluminescent labels (e.g., luminol, isoluminol, aromatic acridinium ester, imadazole, acridinium salt and oxalate ester); (vi) colorimetric labels; (vii) metal colloid labels; (viii) latex and silica particles with dyes incorporated into them; (ix) dyes; and (x) affinity labels (e.g., biotin). The binding and detection of these labels can be done using techniques known to those skilled in the art.

It is then determined if the quantity(ies) of the target marker(s) in the biological sample is(are) indicative of the presence, absence or status of a disease or condition. This is accomplished using any of a variety of well known methods of statistical analysis. For instance, a clustering technique, such as the one exemplified in Example 2, can be used. Alternatively, the determination can be accomplished by comparing the quantity(ies) of the target marker(s) in the sample to the quantity(ies) of the target marker(s) in normal patients. "Normal patients" are those not suffering from the particular disease or condition to be diagnosed or monitored. For instance, the amount of a target marker can be compared to a normal range. This normal range is found by determining the amount of the marker in a large number of samples from normal individuals by the same method (i.e., same type of biological sample, same steps, same reagents, same conditions) as used in assaying the patient sample. If the amount of target marker is outside the normal range, then the presence of the disease or condition is indicated. Alternatively, the amount of a target marker can be compared with a cut-off value that is indicative of the disease or condition. The cut-off value can be determined by testing a large number of samples from normal individuals and from patients known to be suffering from a particular disease or condition of interest. If the amount of target marker exceeds the cut-off, then the disease or condition is indicated. Further, the amount of a target marker and/or the presence of two or more target markers outside their normal ranges or which exceed their cutoffs may also be indicative of the status of disease or condition. In analyzing data, including determining a normal range or cut-off value, standard statistical methods well known in the art can be used. Finally, as can be appreciated, the normal ranges and the cut-off values can be expressed in the units of detection (e.g., levels of absorbance or of fluorescence) as a matter of convenience and ease of making the correlation.

For example, as noted above, the measurement of DA-DKP can be used in the diagnosis or monitoring of MS. DA-DKP levels in normal human patients is in the range of about 50-100 ng/ml. Those skilled in the art will be able to readily determine when the level of DA-DKP is significantly elevated to indicate multiple sclerosis using any of the methods disclosed herein or other known statistical methods.

The above methods of the present invention can be used to diagnose or monitor a number of diseases and conditions. These diseases and conditions include, but not limited to, those identified in Tables 1 and 2.

In a further embodiment, the invention provides objective biochemical markers useful for the diagnosis and monitoring of multiple sclerosis (MS) in patients. In particular, the following markers have been identified in plasma samples by liquid chromatography followed by mass spectrometry (LC-MS):

1. First, a compound of mass 175 (actual mass of 176) has been found to be missing from the plasma of MS patients as compared to plasma samples from normal humans.
2. A compound of mass 145 (actual mass of 146) has also been found to be missing from the plasma of MS patients as compared to plasma samples from normal humans.
3. A compound of mass 185 (actual mass 186) has been found to be significantly elevated in the plasma of MS patients who have active disease as compared to plasma samples from normal humans and from MS patients whose disease is not active. This compound has been identified as the cyclic dipeptide aspartic acid-alanine diketopiperazine (DA-DKP). It is interesting to note that this compound has been shown to inhibit platelet activating factor and to inhibit the production and/or release of interleukin-8 (see PCT application WO 02/11676).
4. A compound of mass 199 (actual mass 200) has been found to be significantly elevated in the plasma of MS patients who have active disease as compared to plasma samples from normal humans and from MS patients whose disease is not active. This compound has been identified as N-acetyl-alanine-serine diketopiperazine (NAS-DKP).

Thus, the absence of one or both of the compounds of masses 175 and 145 from a plasma sample indicates that the patient has MS. A significantly elevated level of one or both of the diketopiperazines of masses 185 and 199 indicates that the patients are suffering from active MS. MS diagnostic compounds include, but are not limited to, all of these compounds and the diketopiperazines and truncated disease-associated proteins of Tables 1 and 2.

"Active MS" is used to mean the period when new, additional or worsening clinical manifestations occur (an attack, exacerbation, flare or relapse). It is usually associated with increased myelin/neuron destruction, elevated white blood cells (>4/hpf) and IgG synthesis rate (>9) in the cerebrospinal fluid, MRI demyelination plaques, and "black holes" which represent neuronal loss.

In yet another embodiment, the invention provides objective biochemical markers useful for the diagnosis or monitoring of Alzheimer's disease. The invention provides methods of diagnosing or monitoring Alzheimer's disease using an Alzheimer's diagnostic compound. The methods are accomplished by obtaining a biological sample from a patient to be diagnosed or monitored and determining the amount of an Alzheimer's diagnostic compound in the biological sample. Alzheimer's diagnostic compounds include, for example: (i) a compound having a mass of about 175 as determined by liquid chromatography and mass spectrometry; and (ii) the diketopiperazine derived from beta-amyloid which is Asp-Ala DKP (MW 186.15). Both diagnostic compounds have been found elevated in the plasma of Alzheimer's patients and are considered diagnostic of the disease. Other Alzheimer's diagnostic compounds include the diketopiperazines and truncated disease-associated proteins of Tables 1 and 2.

In a further embodiment, the invention provides methods for the diagnosis or monitoring of placental ischemia in pregnant patients. These methods comprise obtaining a biological sample from a pregnant patient and measuring the amount of a placental ischemia diagnostic compound, including those derived from pregnancy-associated proteins, in the biological sample. Examples of placental ischemia diagnostic compounds useful in the methods include, for example: (i) Gly-Leu diketopiperazine (GL-DKP) derived from beta-human chlorionic gonadotropin; and (ii) Ala-Pro diketopiperazine (AP-DKP) derived from fetal erythropoietin. Other placental ischemia diagnostic compounds include the diketopiperazines and truncated disease-associated proteins of Tables 1 and 2.

Those skilled in the art will be able to readily isolate and determine the chemical composition of those compounds identified above only by their masses. Once their chemical compositions are known, they can be assayed by methods other than mass spectrometry, including those methods described above, preferably by means of an immunoassay.

In yet another embodiment, the invention provides binding partners useful in the immunoassays described above. Binding partners include antibodies, antiserum or a purified fraction thereof, aptamers and other compounds capable of specifically binding to a target marker. Suitable antibodies include polyclonal antibodies, monoclonal antibodies, bispecific antibodies, humanized antibodies, chimeric antibodies, single-chain antibodies, Fab fragments, F(ab')$_2$ fragments, fragments produced by an Fab expression library, epitope-binding fragments of any of the foregoing, and complementarity determining regions (CDRs). Antibodies suitable for use in the invention can be prepared by known methods. Particularly suitable antibodies are monoclonal antibodies having specificity for the diketopiperazines of the present invention. Since the diketopiperazines are small compounds, they will preferably be attached to an immunogenic carrier molecule for use as an immunogen to prepare antibodies specific to them. Suitable carrier molecules (e.g., KLH) and methods of attaching molecules to them are well known in the art. The immunogen can be used to produce monoclonal antibodies using fusion procedures of Kohler and Milstein, *Nature* 1975 256 pp.495-497, with modifications known to those skilled in the art. The term "isolated" used in connection with binding partner means the binding partner is not within the milieu of its natural environment if found in nature and is not meant to indicate any level of purity of the binding partner.

Aptamers can be used in place of, or in combination with, the antibodies in any of the above described immunoassays. Aptamers are oligonucleotides that are specific for proteins, peptides, derivatives of proteins and peptides, inorganic molecules and other non-nucleotide molecules. See, e.g., PCT applications WO 00/070329, WO 01/79562 and WO 99/54506, and U.S. Pat. No. 5,756,291, which are incorporated herein by reference in their entirety. Aptamers suitable for use in the present invention can be prepared using the methods described in these references. Briefly, a heterogeneous population of oligonucleotides of random sequences is synthesized, and a marker of the invention is mixed with the heterogeneous population of oligonucleotides. Complexes are formed with some, but not all, of the sequences present in the oligonucleotide population. The complexes are isolated, and the oligonucleotides recovered and amplified (e.g., by PCR). The resulting mixture of oligonucleotides can be used as the starting material for another round of complexation, isolation and amplification, and the process will typically be repeated several times until an aptamer of satisfactory specificity is obtained and/or until a consensus aptamer sequence is identified. Suitable labels for aptamers include dyes, enzymes, radioactive labels, etc.

The present invention further provides compositions containing the binding partners described above in a physiologically-acceptable carrier. Such physiologically-acceptable carriers are well known in the art and include, for example, aqueous solutions such as bicarbonate buffers, phosphate buffers, physiological saline, Ringer's solution and the like.

The invention also provides kits for quantifying the target markers. Such kits optionally contain various reagents useful for conducting the methods of the present invention, including one or more binding partners specific for a target marker, a labeled component useful for detecting the target marker, buffers, diluents, standards, controls, etc. The kits can also contain bottles, vials, tubes, syringes, microtiter plates or other solid substrates, instructions and the like.

The following Examples are intended to illustrate the embodiments of the invention and are not intended to limit the invention.

EXAMPLES

Example 1

Diagnosis of Placental Ischemia

The presence of several diketopiperazines has been detected in maternal plasma. Of particular interest are the ones derived from the N-termini of β-human chorionic gonadotropin (βHCG) and fetal erythropoietin. These are glycine-leucine diketopiperazine (GL-DKP) and alanine-proline diketopiperazine (AP-DKP), respectively. AP-DKP, in particular, is elevated in FGR pregnancy due to elevation of fetal erythropoietin in FGR (Teramo, et al., *Acta Obstet. Gynecol. Scand.* 2002. 83(1): p. 245-51; Jazayeri et al., *Am. J. Obstet. Gynecol.*, 2000. 183(1): p. 188-90; Jazayeri et al., *J. Perinatol.*, 1999. 19(4): p. 255-9) and its specific degradation in acidic conditions (protonation of the N-terminal amino acid (Goolcharran and Borchardt, *J. Pharm. Sci.*, 1998. 87(3): p. 283-8) and the relative importance for proline in position 2 of the primary amino acid sequence) to yield AP-DKP.

Subjects for the study were selected from patients referred to a Maternal-Fetal Medicine (MFM) practice with complicated pregnancies. Inclusion criteria for the study were:

Estimated fetal weight <10$^{th}$ percentile for gestational age by ultrasound in addition to:
 an amniotic fluid index (AFI) <8 or,
 a ratio of blood flow velocity during systole to diastole (S/D) in the umbilical artery as measured with pulse-wave Doppler >3 or,
 preeclampsia, as defined by standard clinical criteria.

There were 12 patients in the study group, including 11 singletons and one twin gestation. There were 5 patients in the control group including 1 twin gestation. Gestational ages in the study group at time of delivery were between 26.3-38 weeks with an average gestational age of 30.2 weeks versus 38 weeks in the control group. Average birth weights were 1016 grams in the study groups versus 3114 grams in the control group. Birth weight percentages for the study group averaged <10% versus 43% in the control group. Umbilical artery Doppler flow studies were obtained in 10 of the 12 study patients; of these, all were abnormal, with 2 patients having reversed end-diastolic flow, 6 having absent end-diastolic flow, and 2 having an S/D ratio >3.0. Nine of the 12 study patients had preeclampsia. Two of the 12 study patients had HELLP syndrome.

Recombinant βHCG (Sigma) was incubated in phosphate buffer 0.1M, pH 7.4 at 60° C. for 12 hours and analyzed for the presence of GL-DKP (MW 170.21) by liquid chromatography (LC) followed by ESI+ mass spectrometry (ESI+/MS). The results are presented in FIG. 1.

Figure 3:
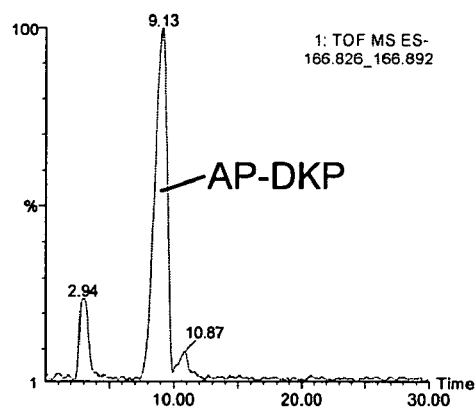
FIG. 3: Printout from a mass spectrometer. The sample was recombinant erythropoietin processed by liquid chromatography followed by mass spectrometry.

Similarly, recombinant erythropoietin (Amgen) was incubated in phosphate buffer 0.1M, pH 7.4 at 60° C. for 12 hours and analyzed for the presence of AP-DKP (MW 168.18) by LC and ESI-/MS. The results are presented in FIG. 3.

Figure 2:
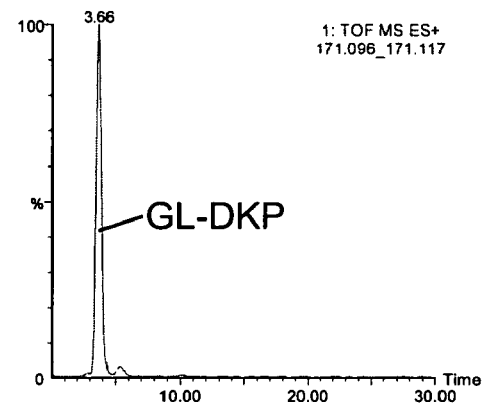
FIG. 2: Printout from a mass spectrometer. The sample was a plasma sample from a pregnant woman (patient 4) processed by liquid chromatography followed by mass spectrometry.
Figure 4:
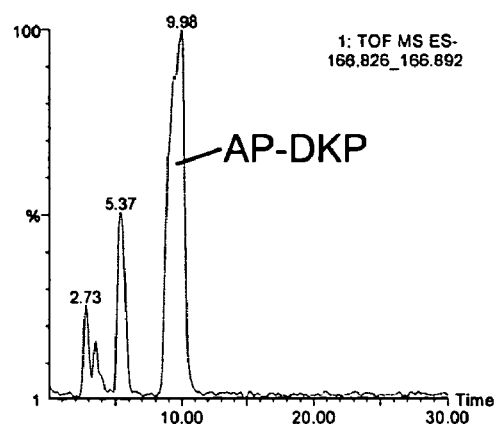
FIG. 4: Printout from a mass spectrometer. The sample was a plasma sample from a pregnant woman (patient 4) processed by liquid chromatography followed by mass spectrometry.

Plasma samples were taken from study group patients and the control group patients and processed by LC followed by ESI/MS. The results for one study group patient (patient 4) are presented in FIGS. 2 and 4. As can be seen, GL-DKP (derived from βHCG) and AP-DKP (derived from fetal erythropoietin) were detected.

Example 2

Classification of MS Patients Using Liquid Chromatography—Mass Spectrometry and Clustering A novel method of determining the Multiple Sclerosis (MS) status of patients is presented here along with some results of a small test set of both MS and normal patients. In the present method, blood samples were collected from both normal and MS patients and analyzed by a liquid chromatography—mass spectrometry (LC-MS) method to determine the concentration of several putative MS markers. The resulting data were analyzed by a mathematical clustering technique that finds natural groupings within the data to see whether there were any simple relationships between the levels of these putative markers and the presence, absence or status of MS.

Patients

Patients with MS were diagnosed by accepted clinical and laboratory standards. Neurological signs and symptoms, magnetic resonance imaging evidence of demyelination, presence of oligoclonal bands in cerebrospinal fluid, white cell enumeration and IgG synthesis rates were used to make the diagnosis. Active disease was defined based on the above in the presence of acute or progressive neurological manifestations.

Sample Preparation

Blood samples were collected in heparinized tubes. The blood samples were separated via centrifugation into plasma and red cells. The red cells were discarded, and the plasma was further refined by passing it through a size exclusion filter (Centricon 3) to remove all components that were greater than 3,000 daltons. The resulting filtrates were analyzed immediately or frozen for later analysis.

LC-MS Method

The samples were run on an HPLC (a Waters 2975 system) to separate the various components. The column used was an Amersham mono-Q anion exchange. The mobile phase was a 50 mM solution of ammonium acetate, pH 6.7, run at 1 ml/min. The flow was split 4:1 post column leaving a 250 ul/min stream which was routed to a Micromass LCT mass spectrometer operated in negative electrospray ionization (ESI-) mode using a cone voltage of 20v. Because of the high flow rate and high aqueous content of the solvent, the desolvation temperature was set to 400° C. Standards of DA-DKP and EA-DKP were run with each set of data to calibrate for transient differences in instrument sensitivity. The standard concentrations used are 500, 100, 20, and 4 ng/ml of each DKP. Detection of the DKPs by the mass spectrometer was found to be linear in this range of concentrations ($r2>0.998$).

Data Preparation

While there are no calibrants for some of the putative markers described below, it was assumed that the sensitivity of the instrument was linear across the spectrum and, thus, all masses for which there was no calibrant were normalized to the level of 500 ng/ml DA-DKP.

Mathematical Analysis

Clustering is a classification technique that identifies groups of similar objects where similarity is derived solely on the basis of the variables that describe the data. Ideally, the groups are formed in such a way that objects within a group are similar to each other, while objects in different groups as are as dissimilar as possible.

When one tries to cluster raw data from experimental data whose variables are poorly scaled, components with large magnitude will dominate any distance metric, resulting in a disproportionate weighting of those variables. Since one has no a priori knowledge of each variable's importance, one scales to give equal weight to each of the variables. Dimensional scaling is employed so each variable is shifted and scaled. As a result, the means are zero and the variances are equal.

Often, experiments generate high-dimensional data sets which may have strong dependencies. In order to maximize the likelihood of a nontrivial classification, one wishes to minimize the number of dimensions by extracting the most relevant information from the data while minimizing noise. Methods of feature extraction include wavelet decomposition, Fourier transformation, factor analysis and independent component analysis.

In this work, feature extraction was performed using a variant of factor analysis called principal component analysis (PCA). In PCA, the data are represented as coefficients of the eigenvectors of the covariance matrix that describes the data. Moreover, the relative strengths of each of the eigenvectors (also known as principal components) are given by the eigenvalues. Eigenvectors with corresponding eigenvalues that are below some threshold can often be omitted as noise.

After choosing a set of 10 putative masses for analysis, the data were analyzed with a clustering toolset in Matlab written by Raphael Bar-Or, DMI BioSciences, Inc., Englewood, Colo. Other suitable clustering software is available commercially. Trial and error analysis revealed that 2 masses of 185 and 199 appearing early in the runs had some power to separate the data into 2 groups, one of which is active MS and the other non-active MS and normals. In a subset of MS patients and normal patients, the settings of the clustering toolkit were optimized to achieve good separation between active MS and all other diagnoses. The settings for this analysis are given in Table 4.

Figure 5:
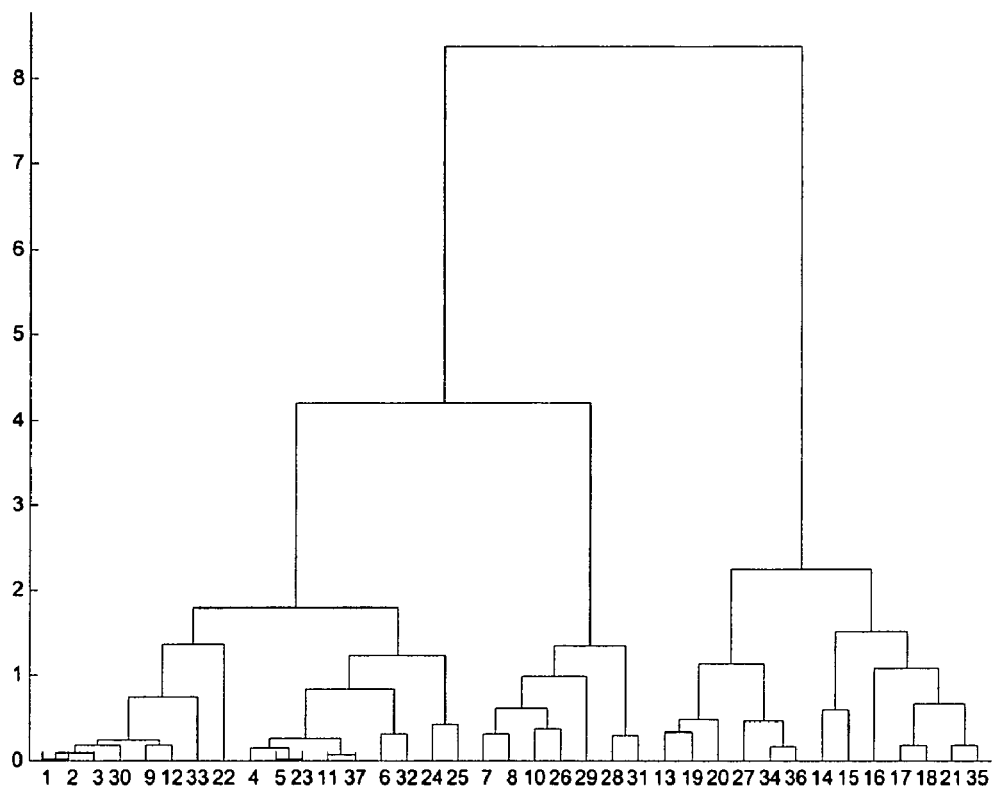
FIG. 5: A clustering dendogram.

Samples from a total of 37 patients were run. Of these, 24 were in cluster #1 (8 normals and 16 non-active MS), and 13 were in cluster #2 (active MS). There appear to be few, if any, misclassifications, and an inspection of the clustering dendrogram (FIG. 5) reveals that the space is quite separable, meaning that there is sufficient space between the clusters so that this separation is not likely to be the product of chance alone. A small bootstrap (leave-one-out analysis) confirmed that the separation is indeed stable (95% by Rand's Statistic).

The groups found by the clustering method were used as a classifier. In this small data set, a sensitivity of 100% and a specificity of 84.6% for active MS were found.

The two masses of 185 and 199 were identified to be Asp-Ala DKP (DA-DKP) and N-acetyl-Ala-Ser DKP (NAS-DKP), respectively. These two DKPs are the degradation products of two important central nervous system proteins, namely beta amyloid and myelin basic protein (see Table 1).

It was noted that a marker labeled "175@8.5 mins" appears to be deficient in all of the suspected MS patients and unusually high in Alzheimer's patients. A similar pattern was observed in another mass labeled "145@12.7 mins". Addition of this variable to the clustering analysis would surely improve the separation, but data beyond 6 minutes is available for only a small subset of patients (only 14 samples were run for longer than 6 minutes, and only 10 of these had also been run for the shorter time). An analysis of this smaller group revealed that a simple threshold on the level of "175@8.5 mins" was sufficient to quite accurately separate MS from normals and non-MS patients without distinguishing between the active and non-active forms. While there is insufficient data to conclude that this 175 marker is definitive, the evidence suggests that, together with the two markers (185 and 199) used in the above clustering analysis, there is a strong likelihood for an algorithm that can accurately separate MS patients from normals and non-MS patients and that the MS patients can be further categorized into active and non-active MS.

TABLE 4

```
%***********************************************
%**** EDIT THE VALUES IN THIS BLOCK *************
%***********************************************
standout=[];
% elements to color differently so that they stand out
logdata=1;
% convert to log data
scaling=0;
% 1 = dimensional scaling
% 0 = no dimensional scaling
numberOfClusters=2;
% the number of desired clusters (should be =>2)
convertPca=1;
% 1 = convert to pca space
% 0 = no conversion (original space)
keepVariation=0.95;
% the amount of variability to keep in the pca conversion
clusterAlgorithm='hierarchical';
% type of clustering desired options are:
% 'kplane'
% 'kmeans'
% 'kmedians'
% 'fuzzy_cmeans'
% 'hierarchical'
% 'gravity'
gravorder=15;
% only applicable if cluster type is gravity
gravtol=2e-3;
% only applicable if cluster type is gravity
addmasses=1;
% only applicable if cluster type is gravity
heirarchicalMetric='Euclid';
% n/a if clusterAlgorithm is not 'hierarchical' or 'permutation'
% options are:
% 'Euclid'=Euclidean distance (default)
% 'SEuclid'=Standardized Euclidean distance
% 'Mahal'=Mahalanobis distance
% 'CityBlock'=City Block metric
% 'Minkowski'=Minkowski metric
% 'Correlation'=1-Correlation Coefficients
heirarchicalLinkage='ward';
%'single'=Shortest distance
%'complete'=Largest distance
%'average'=Average distance
%'centroid'=Centroid distance (approximate, computed using a formula that is exact if Y contains Euclidean distances)
%'ward'=Incremental sum of squares
displayClusterInfo=1;
% 1 = display cluster info
% 0 = no cluster info display
displayScatterplot=1;
% 1 = display scatterplot of first three components
% 0 = no scatterplot
displayClusterGeneResponse=1;
% 1 = display gene response representation for each cluster
% 0 = no display
typeResponseRep='line';
% n/a if displayClusterGeneResponse is disabled
% options are:
% 'box'
```

TABLE 4-continued

```
% 'line'
% 'bar'
% 'area'
crossValidation=0;
% leave one out cross-validation (can take a VERY long time)
% 1 = do cross validation
% 0 = no cross validation
```

Example 3

Analysis of an MS Patient Using Liquid Chromatography—Mass Spectrometry

A blood sample was collected from an MS patient with active MS and processed and analyzed by LC-MS as described in Example 2. The following DKP's were found: DA-DKP (from N-terminus of beta-amyloid), NAS-DKP (from N-terminus of myelin basic protein), N-acetyl-Ala Phospho-Ser DKP (from N-terminus of myelin basic protein), Gln-Asn DKP (from C-terminus of beta-amyloid) and Arg-Arg DKP (from C-terminus of myelin basic protein).

Example 4

Diagnosis of Alzheimer's Disease

As noted in Example 2, a marker labeled "175@8.5 mins" was found to be present in unusually high amounts in the plasma of Alzheimer's patients. It is expected that this marker will be useful in the diagnosis of Alzheimer's disease.

In addition, a marker at mass 186.15, which DA-DKP, has been found elevated in the plasma of Alzheimer's patients. It appears to be diagnostic of the disease.

Finally, another possible marker of mass 200 (actual mass 201) has been found. It has not yet been identified, but a likely candidate is NAS-DKP.

The above description of the invention, including the Examples, is intended to be merely illustrative of the invention and is not intended to limit the invention. Various changes and modifications can be made by those skilled in the art without departing from the spirit and scope of the invention.

We claim:

1. A method of diagnosing multiple sclerosis (MS) comprising the steps of:
    (a) obtaining a biological sample from a patient, wherein the biological sample is serum, plasma or blood;
    (b) measuring the amount of one or more MS diagnostic compounds in the biological sample, the MS diagnostic compound(s) being:
        (i) aspartic acid-alanine diketopiperazine (DA-DKP);
        (ii) N-acetyl-alanine-serine diketopiperazine (NAS-DKP); or
        (iii) both of the foregoing;
    wherein
    an elevated amount of DA-DKP, NAS-DKP or both DA-DKP and NAS-DKP in the biological sample is indicative of active MS.

2. The method of claims 1 wherein the biological sample is serum or plasma.

3. The method of claim 2, wherein the biological sample is plasma.

4. The method of claim 2, wherein the biological sample is serum.

5. The method of any one of claims 1 and 2-4 wherein step (b) is conducted by mass spectrometry, immunoassay or both.

* * * * *

UNITED STATES PATENT AND TRADEMARK OFFICE
CERTIFICATE OF CORRECTION

PATENT NO. : 7,575,929 B2  Page 1 of 1
APPLICATION NO. : 10/679699
DATED : August 18, 2009
INVENTOR(S) : Bar-Or et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 642 days.

Signed and Sealed this

Fourteenth Day of December, 2010

David J. Kappos
*Director of the United States Patent and Trademark Office*